US011370744B2

(12) United States Patent
Nakayama et al.

(10) Patent No.: US 11,370,744 B2
(45) Date of Patent: Jun. 28, 2022

(54) COMPOUND, CURABLE COMPOSITION, CURED PRODUCT, OPTICAL MEMBER, AND LENS

(71) Applicant: FUJIFILM Corporation, Tokyo (JP)

(72) Inventors: Takafumi Nakayama, Kanagawa (JP); Naoyuki Morooka, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 344 days.

(21) Appl. No.: 16/784,163

(22) Filed: Feb. 6, 2020

(65) Prior Publication Data

US 2020/0181061 A1 Jun. 11, 2020

Related U.S. Application Data

(63) Continuation of application No. PCT/JP2018/030318, filed on Aug. 15, 2018.

(30) Foreign Application Priority Data

Aug. 18, 2017 (JP) .............................. JP2017-158122

(51) Int. Cl.
| C07C 69/017 | (2006.01) |
| C07C 69/54 | (2006.01) |
| C07D 241/38 | (2006.01) |
| C08F 12/34 | (2006.01) |
| C08F 22/20 | (2006.01) |
| C08F 22/22 | (2006.01) |
| G02B 1/04 | (2006.01) |
| C08F 22/10 | (2006.01) |

(52) U.S. Cl.
CPC ............ *C07C 69/54* (2013.01); *C07D 241/38* (2013.01); *C08F 22/20* (2013.01); *C08F 22/22* (2013.01); *G02B 1/04* (2013.01); *G02B 1/041* (2013.01); *C07C 69/017* (2013.01); *C07C 2603/40* (2017.05); *C08F 12/34* (2013.01); *C08F 22/1006* (2020.02)

(58) Field of Classification Search
None
See application file for complete search history.

(56) References Cited

U.S. PATENT DOCUMENTS

| 2013/0237630 A1 | 9/2013 | Morooka et al. |
| 2015/0197592 A1* | 7/2015 | Someya ................ G02B 1/041 560/194 |

(Continued)

FOREIGN PATENT DOCUMENTS

| CN | 104684946 A | 6/2015 |
| CN | 106103497 A | 11/2016 |

(Continued)

OTHER PUBLICATIONS

International Search Report issued in PCT/JP2018/030318; dated Oct. 16, 2018.
International Preliminary Report On Patentability and Written Opinion issued in PCT/JP2018/030318; dated Feb. 18, 2020.
An Office Action mailed by China National Intellectual Property Administration dated May 28, 2021, which corresponds to Chinese Patent Application No. 201880052088.8 and is related to U.S. Appl. No. 16/784,163; with Englist language translation.
An Office Action; "Notice of Reasons for Refusal", mailed by the Japanese Patent Office dated Jan. 5, 2021, which corresponds to Japanese Patent Application No. 2019-536781 and is related to U.S. Appl. No. 16/784,163; with English language translation.

*Primary Examiner* — Richard A Huhn
(74) *Attorney, Agent, or Firm* — Studebaker & Brackett PC

(57) ABSTRACT

According to the present invention, as a monomer which is unlikely to be crystallized in a curable composition for manufacturing an optical member and which enables manufacture of a cured product having a high level of moisture-heat resistance, a compound represented by General Formula (A) is provided.

General Formula (A)

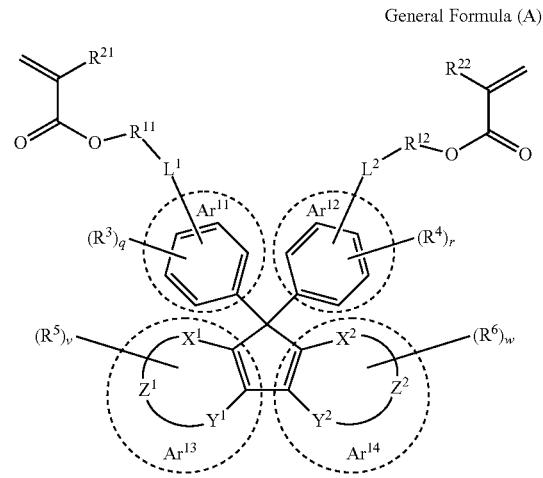

In the formula, $Ar^{11}$ and $Ar^{12}$ each independently represent an aryl group or a heteroaryl group; $X^1$, $Y^1$, $X^2$, $Y^2$, $Z^1$, and $Z^2$ each independently represent a nitrogen atom or a carbon atom, or the like; $Ar^{13}$ and $Ar^{14}$ each independently represent an arylene group or a heteroarylene group, where at least one of $Ar^{13}$ or $Ar^{14}$ is a group other than a phenylene group; $R^3$ to $R^6$ each independently represent a substituent, q and r each independently are an integer of 0 to 4, and v and w each independently are an integer of 0 or more; $L^1$ and $L^2$ each independently represent a single bond, an oxygen atom, an ester bond, or the like; $R^{11}$ and $R^{12}$ each independently represent a divalent linking group containing a branched alkylene group; and $R^{21}$ and $R^{22}$ each independently represent a hydrogen atom or a methyl group.

20 Claims, No Drawings

(56) References Cited

U.S. PATENT DOCUMENTS

| | | | |
|---|---|---|---|
| 2017/0002124 | A1 | 1/2017 | Ishiyama et al. |
| 2017/0342181 | A1 | 11/2017 | Morooka |
| 2018/0305486 | A1* | 10/2018 | Nakayama ............. G02B 1/041 |

FOREIGN PATENT DOCUMENTS

| | | |
|---|---|---|
| CN | 106397752 A | 2/2017 |
| JP | 2009-126011 A | 6/2009 |
| JP | 2012-107191 A | 6/2012 |
| JP | 5372492 B2 | 12/2013 |
| JP | 2014-080572 A | 5/2014 |
| JP | 2015-199952 A | 11/2015 |
| JP | 2017-036249 A | 2/2017 |
| WO | 2016/140245 A1 | 9/2016 |
| WO | 2017/115649 A1 | 7/2017 |

\* cited by examiner

COMPOUND, CURABLE COMPOSITION, CURED PRODUCT, OPTICAL MEMBER, AND LENS

CROSS-REFERENCE TO RELATED APPLICATIONS

This application is a continuation of PCT International Application No. PCT/JP2018/030318 filed on Aug. 15, 2018, which claims priority under 35 U.S.C § 119 (a) to Japanese Patent Application No. 2017-158122 filed on Aug. 18, 2017, the entire content of which is incorporated herein by reference.

BACKGROUND OF THE INVENTION

1. Field of the Invention

The present invention relates to a compound, a curable composition, a cured product, an optical member, and a lens.

2. Description of the Related Art

Conventionally, a glass material has been used for an optical member of an imaging module such as a camera, a video camera, a mobile phone with a camera, a video phone, or a door phone with a camera. Glass materials have been used preferably because they have various optical characteristics and excellent environmental resistance, but they have a disadvantage in that weight reduction and miniaturization are not easy and workability or productivity is poor. In contrast, since a resin cured product can be produced in a massive amount and has excellent workability, the resin cured product has recently been used in various optical members.

In recent years, in accordance with miniaturization of an imaging module, a size of an optical member used in the imaging module is required to be reduced, but in a case of miniaturizing an optical member, a problem of chromatic aberration occurs. It is possible to correct chromatic aberration by allowing a resin cured product forming an optical member to have a small Abbe number.

JP2015-199952A, WO2017/115649A, and JP2014-080572A disclose a compound having a bis(aryl)fluorene skeleton or a skeleton similar thereto as a monomer used for forming the above-mentioned resin cured product.

JP2015-199952A discloses that by using a (meth)acrylate compound having a bis(aryl)fluorene skeleton, it is possible to obtain a curable composition which has excellent handleability characteristics without using a diluent, and which enables a high refractive index to be compatible with scratch resistance in a cured product. WO2017/115649A discloses that by using a compound having a heteroaryl group in a bis(aryl)fluorene-like skeleton, it is possible to obtain a curable composition that enables formation of a cured product having a small Abbe number. JP2014-080572A discloses that by using a compound having a fused aromatic ring group in a bis(aryl)fluorene-like skeleton and a non-conjugated-vinylidene-group-containing compound, it is possible to obtain a curable composition that enables formation of a cured product having a small Abbe number.

SUMMARY OF THE INVENTION

In the case of the compound disclosed in JP2015-199952A, a cured product has a high saturated water absorption of 1.55%, and therefore there is still room for improvement in moisture-heat resistance. In addition, in a case where a composition containing a high concentration of a compound having a bis(aryl)fluorene skeleton or a skeleton similar thereto is used in manufacture of an optical member using the compounds disclosed in JP2015-199952A, WO2017/115649A, and JP2014-080572A, a cured product having a smaller Abbe number is easily obtained. However, a curable composition containing a high concentration of a monomer having the above-mentioned skeleton easily becomes highly viscous or is easily crystallized, and this may affect handleability during molding and quality of a cured product to be obtained. Furthermore, the above-mentioned curable composition easily changes its moldability after long-term storage, particularly at low temperatures or the like.

An object of the present invention is to provide a monomer which is unlikely to be crystallized in a case where it is prepared as a curable composition for manufacturing an optical member, and which enables manufacture of a cured product having a high level of moisture-heat resistance. In particular, an object of the present invention is to provide a compound which has a bis(aryl)fluorene-like skeleton and is unlikely to be crystallized in a case where it is prepared as a curable composition. Another object of the present invention is to provide a curable composition that hardly changes its formability after long-term storage.

Specific means for achieving the above-described objects are as follows.

[1] A compound represented by General Formula (A):

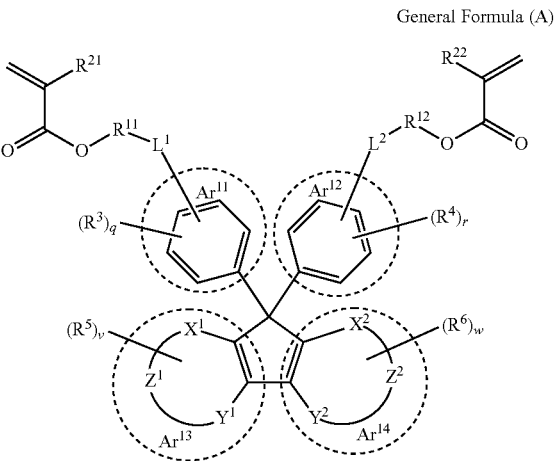

General Formula (A)

In General Formula (A), $Ar^{11}$ and $Ar^{12}$ each independently represent an aryl group containing a benzene ring surrounded by a broken line or a heteroaryl group containing a benzene ring surrounded by a broken line as one of rings constituting a fused ring, $X^1$, $Y^1$, $X^2$, and $Y^2$ each independently represent an oxygen atom, a sulfur atom, a nitrogen atom, or a carbon atom; $Z^1$ represents an atomic group which forms a 5- to 7-membered aromatic ring together with $X^1$—C=C—$Y^1$, and which contains at least one selected from an oxygen atom, a sulfur atom, a nitrogen atom, or a carbon atom; and $Z^2$ represents an atomic group which forms a 5- to 7-membered aromatic ring together with $X^2$—C=C—$Y^2$, and which contains at least one selected from an oxygen atom, a sulfur atom, a nitrogen atom, or a carbon atom, $Ar^{13}$ and $Ar^{14}$ each independently represent an arylene group containing an aromatic ring surrounded by a broken line or a heteroarylene group containing an aromatic ring surrounded by a broken line, where at least one of $Ar^{13}$ or $Ar^{14}$ is a group other than a phenylene group, $R^3$ to $R^6$ each independently represent a substituent; q and r each independently are an integer of 0 to 4; v is an integer of 0 or more, where a maximum number of v is a maximum number of substituents capable of being substituted on the ring formed by $X^1$—C=C—$Y^1$ and $Z^1$; and w is an integer of 0 or more, where a maximum number of w is a maximum number of substituents capable of being substituted on the ring formed by $X^2$—C=C—$Y^2$ and $Z^2$, $L^1$ and $L^2$ each independently represent a single bond, an oxygen atom, a sulfur atom, or an ester bond, $R^{11}$ and $R^{12}$ each independently represent a divalent linking group containing a branched alkylene group in which one or more alkyl groups are substituted on a linear alkylene group, $R^{21}$ and $R^{22}$ each independently represent a hydrogen atom or a methyl group, and in a case where $Ar^{11}$ to $Ar^{14}$ each independently are a fused ring group containing an aromatic ring surrounded by a broken line as one of rings constituting the fused ring, a group having $L^1$ as a linking group, a group having $L^2$ as a linking group, and $R^3$ to $R^6$ each independently may be substituted on the aromatic ring surrounded by the broken line, or may be substituted on another ring constituting the fused ring than the aromatic ring surrounded by the broken line.

[2] The compound according to [1], in which $Ar^{11}$ and $Ar^{12}$ each are a phenyl group.

[3] The compound according to [1] or [2], in which at least one of $Ar^{13}$ or $Ar^{14}$ is a fused ring group containing the aromatic ring surrounded by the broken line as one of the rings constituting the fused ring.

[4] The compound according to any one of [1] to [3], in which $X^1$ and $Y^1$, or $X^2$ and $Y^2$ each are a nitrogen atom.

[5] The compound according to any one of [1] to [4], in which at least one of $L^1$ or $L^2$ is an ester bond.

[6] The compound according to any one of [1] to [5], in which the branched alkylene group is a mixture of structural isomers in which positions at which the one or more alkyl groups are substituted on the linear alkylene group are different.

[7] A curable composition comprising the compound according to any one of [1] to [6].

[8] The curable composition according to [7], further comprising a non-conjugated-vinylidene-group-containing compound.

[9] The curable composition according to [7] or [8], further comprising a hydroperoxide compound as a thermal radical polymerization initiator.

[10] A semi-cured product of the curable composition according to any one of [7] to [9], in which a complex viscosity at 25° C. and a frequency of 10 Hz is $10^5$ to $10^8$ mPa·s.

[11] A cured product of the curable composition according to any one of [7] to [9].

[12] An optical member comprising the cured product according to [11].

[13] A lens comprising the cured product according to [11].

According to the present invention, a compound having a bis(aryl)fluorene-like skeleton, which is a monomer unlikely to be crystallized in a case where it is prepared as a curable composition, is provided. By using the compound having a bis(aryl)fluorene-like skeleton of the present invention, it is possible to provide a curable composition that hardly changes its formability after long-term storage.

DESCRIPTION OF THE PREFERRED EMBODIMENTS

Hereinafter, the present invention will be described in detail. The description of constituent elements described below can be made based on representative embodiments and specific examples, but the present invention is not limited to such embodiments. Numerical value ranges expressed using "to" in the present specification mean a range including numerical values described before and after "to" as the lower limit and the upper limit.

In the present specification, "(meth)acrylate" refers to any one or both of acrylate and methacrylate, and "(meth)acryloyl" refers to any one or both of acryloyl and methacryloyl. A monomer other than a compound represented by General Formula (A) in the present invention is a compound that is distinguished from oligomers and polymers and has a weight-average molecular weight of 1,000 or less.

In addition, in the indication of a group in the present specification, the indication not including substitution or unsubstitution includes a group having a substituent and also a group not having a substituent. For example, an "alkyl group" refers not only to an alkyl group not having a substituent (unsubstituted alkyl group) but also an alkyl group having a substituent (substituted alkyl group).

(Compound Represented by General Formula (A))

General Formula (A)

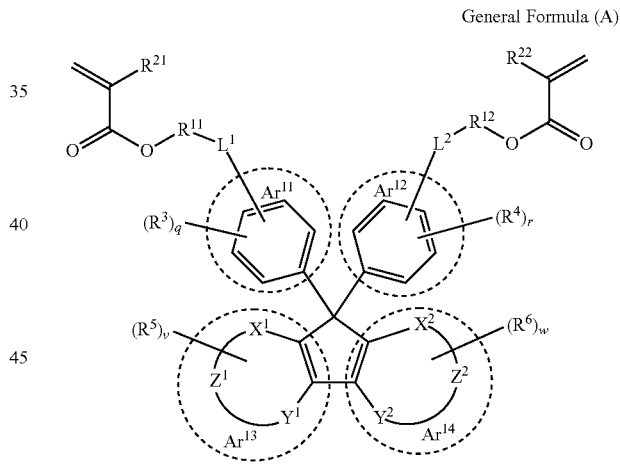

In General Formula (A), $Ar^{11}$ and $Ar^{12}$ each independently represent an aryl group containing a benzene ring surrounded by a broken line or a heteroaryl group containing a benzene ring surrounded by a broken line as one of rings constituting a fused ring, $X^1$, $Y^1$, $X^2$, and $Y^2$ each independently represent an oxygen atom, a sulfur atom, a nitrogen atom, or a carbon atom; $Z^1$ represents an atomic group which forms a 5- to 7-membered aromatic ring together with $X^1$—C=C—$Y^1$, and which contains at least one selected from an oxygen atom, a sulfur atom, a nitrogen atom, or a carbon atom; and $Z^2$ represents an atomic group which forms a 5- to 7-membered aromatic ring together with $X^2$—C=C—$Y^2$, and which contains at least one selected from an oxygen atom, a sulfur atom, a nitrogen atom, or a carbon atom, $Ar^{13}$ and $Ar^{14}$ each independently represent an arylene group containing an aromatic ring surrounded by a broken line or a heteroarylene group containing an aromatic ring surrounded by a broken line, where at least one of $Ar^{13}$ or $Ar^{14}$ is a group other than a phenylene group, $R^3$ to $R^6$ each independently represent a substituent; q and r each independently are an integer of 0 to 4; v is an integer of 0 or more, where a maximum number of v is a maximum number of substituents capable of being substituted on the ring formed by $X^1$—C=C—$Y^1$ and $Z^1$; and w is an integer of 0 or more, where a maximum number of w is a maximum number of substituents capable of being substituted on the ring formed by $X^2$—C=C—$Y^2$ and $Z^2$, $L^1$ and $L^2$ each independently represent a single bond, an oxygen atom, a sulfur atom, or an ester bond, $R^{11}$ and $R^{12}$ each independently represent a divalent linking group containing a branched alkylene group in which one or more alkyl groups are substituted on a linear alkylene group, $R^{21}$ and $R^{11}$ each independently represent a hydrogen atom or a methyl group, and in a case where $Ar^{11}$ to $Ar^{14}$ each independently are a fused ring group containing an aromatic ring surrounded by a broken line as one of rings constituting the fused ring, a group having $L^1$ as a linking group, a group having $L^2$ as a linking group, and $R^3$ to $R^6$ each independently may be substituted on the aromatic ring surrounded by the broken line, or may be substituted on another ring constituting the fused ring than the aromatic ring surrounded by the broken line.

In General Formula (A), $Ar^{11}$ and $Ar^{12}$ each independently represent an aryl group containing a benzene ring surrounded by a broken line or a heteroaryl group containing a benzene ring surrounded by a broken line as one of rings constituting a fused ring. $Ar^{11}$ and $Ar^{12}$ each independently are preferably an aryl group containing a benzene ring surrounded by a broken line. In a case where $Ar^{11}$ and $Ar^{12}$ are aryl groups containing a benzene ring surrounded by a broken line, the aryl group is preferably an aryl group having 6 to 18 carbon atoms, is more preferably an aryl group having 6 to 14 carbon atoms, and is particularly preferably an aryl group having 6 to 10 carbon atoms. In addition, the aryl group may be a monocyclic group or a fused ring group (an aryl group including an aromatic ring surrounded by a broken line as one of rings constituting a fused ring). Examples of the aryl group that is a monocyclic group include a phenyl group, and examples of the aryl group that is a fused ring group include a naphthyl group (a 2-naphthyl group or a 1-naphthyl group). Among them, $Ar^{11}$ and $Ar^{12}$ each independently are particularly preferably a phenyl group composed of only a benzene ring surrounded by a broken line. In a case where $Ar^{11}$ and $Ar^{12}$ are a heteroaryl group containing a benzene ring surrounded by a broken line as one of the rings constituting the fused ring, the heteroaryl group is preferably a heteroaryl group having 9 to 14 ring members, and is more preferably a heteroaryl group having 9 or 10 ring members. In a case where $Ar^{11}$ and $Ar^{12}$ are a heteroaryl group containing a benzene ring surrounded by a broken line as one of the rings constituting the fused ring, examples of heteroatoms include a nitrogen atom, an oxygen atom, and a sulfur atom.

In General Formula (A), $X^1$, $Y^1$, $X^2$, and $Y^2$ each independently are an oxygen atom, a sulfur atom, a nitrogen atom, or a carbon atom. All of $X^1$, $Y^1$, $X^2$, and $Y^2$ may be a carbon atom, and all of $X^1$, $Y^1$, $X^2$, and $Y^2$ may be an atom (at least one selected from an oxygen atom, a sulfur atom, or a nitrogen atom) other than a carbon. In addition, a part of $X^1$, $Y^1$, $X^2$, and $Y^2$ may be at least one selected from an oxygen atom, a sulfur atom, or a nitrogen atom, and the remainder may be a carbon atom. For example, any one of $X^1$, $Y^1$, $X^2$, or $Y^2$ may be at least one selected from an oxygen atom, a sulfur atom, or a nitrogen atom, and the remainder may be a carbon atom. Furthermore, any two of $X^1$, $Y^1$, $X^2$, or $Y^2$ (for example, $X^1$ and $Y^1$, or $X^2$ and $Y^2$) may respectively be at least one selected from an oxygen atom, a sulfur atom, or a nitrogen atom, and the remainder may be a carbon atom.

In a case where $X^1$, $Y^1$, $X^2$, or $Y^2$ is at least one selected from an oxygen atom, a sulfur atom, or a nitrogen atom, a nitrogen atom is preferable. For example, $X^1$ and $Y^1$, or $X^2$ and $Y^2$ are preferably a nitrogen atom. In this case, the remaining $X^1$ and $Y^1$, or $X^2$ and $Y^2$ may be, for example, a carbon atom.

$Z^1$ represents an atomic group which forms a 5- to 7-membered aromatic ring together with $X^1$—C=C—$Y^1$, and which contains at least one selected from an oxygen atom, a sulfur atom, a nitrogen atom, or a carbon atom; and $Z^2$ represents an atomic group which forms a 5- to 7-membered aromatic ring together with $X^2$—C=C—$Y^2$, and which contains at least one selected from an oxygen atom, a sulfur atom, a nitrogen atom, or a carbon atom. $Z^1$ and $Z^2$ each independently are preferably an atomic group containing a carbon atom, and are more preferably an atomic group composed of a carbon atom. In addition, $Z^1$ is preferably an atomic group that forms a 5- or 6-membered aromatic ring together with $X^1$—C=C—$Y^1$, and is more preferably an atomic group that forms a 6-membered aromatic ring. $Z^2$ is preferably an atomic group that forms a 5- or 6-membered aromatic ring together with $X^2$—C=C—$Y^2$, and is more preferably an atomic group that forms a 6-membered aromatic ring.

In General Formula (A), $Ar^{13}$ and $Ar^{14}$ each independently represent an arylene group containing an aromatic ring surrounded by a broken line or a heteroarylene group containing an aromatic ring surrounded by a broken line. Where, the arylene group is preferably an arylene group having 6 to 18 carbon atoms, is more preferably an arylene group having 6 to 14 carbon atoms, and is particularly preferably an arylene group having 6 to 10 carbon atoms. The arylene group may be a monocyclic group or a fused ring group (an arylene group including an aromatic ring surrounded by a broken line as one of rings constituting a fused ring). In addition, the heteroarylene group is preferably a heteroarylene group having 5 to 14 ring members, and is more preferably a heteroarylene group having 6 to 10 ring members. The heteroarylene group may be a monocyclic group or a fused ring group (a heteroarylene group including an aromatic ring surrounded by a broken line as one of rings constituting a fused ring). Examples of hetero atoms of the heteroarylene group include a nitrogen atom, an oxygen atom, and a sulfur atom. In a case where $Ar^{13}$ and $Ar^{14}$ are a heteroarylene group containing an aromatic ring surrounded by a broken line as one of the rings constituting the fused ring, the heteroarylene group is preferably a heteroarylene group having 9 to 14 ring members, and is more preferably a heteroarylene group having 9 or 10 ring members.

Where, at least one of $Ar^{13}$ or $Ar^{14}$ is a group other than a phenylene group. That is, at least one of $Ar^{13}$ or $Ar^{14}$ is a fused ring group or a heteroarylene group. At least one of $Ar^{13}$ or $Ar^{14}$ is preferably a fused ring group. Examples of fused ring groups include a naphthylene group (a divalent group obtained by removing two hydrogen atoms bonded to a carbon adjacent to naphthalene). In addition, the fused ring preferably contains a hetero atom, and preferable examples of hetero atoms include a nitrogen atom. $Ar^3$ and $Ar^{14}$ are preferably not the same group. In General Formula (A), it is particularly preferable that any one of $Ar^{13}$ or $Ar^{14}$ be a group other than a phenylene group, and the other one be a phenylene group.

In General Formula (A), $R^3$ to $R^6$ each independently represent a substituent. The substituents represented by $R^3$ to $R^6$ are not particularly limited, and examples thereof include a halogen atom, a halogenated alkyl group, an alkyl group, an alkenyl group, an acyl group, a hydroxyl group, a hydroxyalkyl group, an alkoxy group, an aryl group, a heteroaryl group, an aliphatic cyclic group, a cyano group, and the like. The substituents represented by $R^3$ to $R^6$ are preferably a halogen atom, an alkyl group, an alkoxy group, an aryl group, or a cyano group; are more preferably a halogen atom, an alkyl group having 1 to 5 carbon atoms, an alkoxy group having 1 to 5 carbon atoms, a phenyl group, or a cyano group; and are particularly preferably a halogen atom, a methyl group, a methoxy group, a phenyl group, or a cyano group. Among them, $R^3$ and $R^4$ each independently are preferably a methyl group or a methoxy group. In addition, $R^5$ is preferably a halogen atom, a methyl group, or a methoxy group, and $R^6$ is preferably a halogen atom, a methyl group, a methoxy group, or a cyano group. By incorporating the above-mentioned substituents as $R^5$ and $R^6$, a cured product formed from the curable composition containing the compound represented by General Formula (A) can have a small Abbe number.

q and r each independently are an integer of 0 to 4, are preferably an integer of 0 to 3, and are more preferably an integer of 0 to 2. In addition, v is an integer of 0 or more, where a maximum number of v is a maximum number of substituents capable of being substituted on the ring formed by $X^1$—C═C—$Y^1$ and $Z^1$. v is preferably an integer of 0 to 3, and is more preferably an integer of 0 to 2. w is an integer of 0 or more, where a maximum number of w is a maximum number of substituents capable of being substituted on the ring formed by $X^2$—C═C—$Y^2$ and $Z^2$. w is preferably an integer of 0 to 3, and is more preferably an integer of 0 to 2. All of q, r, v, and w may be 0. Furthermore, in a case where q is an integer of 2 to 4, a plurality of $R^3$'s may be the same as or different from each other, and in a case where r is an integer of 2 to 4, a plurality of $R^4$'s may be the same as or different from each other. In a case where v is an integer of 2 or more, a plurality of $R^5$'s may be the same as or different from each other, and in a case where w is an integer of 2 or more, a plurality of $R^6$'s may be the same as or different from each other.

In General Formula (A), $L^1$ and $L^2$ each independently represent a single bond, an oxygen atom, a sulfur atom, or an ester bond. The ester bond may be either —O—C(═O)— or —C(═O)—O—, but oxygen is preferably bonded to the $Ar^{11}$ side or $Ar^{12}$ side. $L^1$ and $L^2$ each independently are preferably an oxygen atom, a sulfur atom, or an ester bond, and are more preferably an oxygen atom or an ester bond. In a case where $L^1$ or $L^2$ is an ester bond, a substituent is bonded to at least one of two carbons adjacent to a carbon in $Ar^{11}$ or $Ar^{12}$ to which $L^1$ or $L^2$ which is an ester bond is bonded or is preferably bonded to both thereof. For example, in a case where $L^1$ and $L^2$ which are an ester bond are respectively bonded to $Ar^{11}$ and $Ar^{12}$ which are a phenyl group, the phenyl group preferably has a substituent at the ortho position of $L^1$ and $L^2$.

$R^{11}$ and $R^{12}$ each independently represent a divalent linking group containing a branched alkylene group in which one or more alkyl groups are substituted on a linear alkylene group. The carbon number of the linear alkylene group is preferably 2 to 10, is more preferably 2 to 8, is even more preferably 2 to 5, and is particularly preferably 2 to 4. The carbon number of the alkyl group is preferably 1 to 4, is more preferably 1 to 3, is even more preferably 1 or 2, and is particularly preferably 1. The alkyl group may be a linear alkyl group or a branched alkyl group. It is sufficient for the number of substitutions of the alkyl group by the linear alkylene group to be one or more. In a case where the number of substitutions is two or more, two or more alkyl groups may be substituted by the same carbon, or may be substituted by different carbons. In addition, two or more alkyl groups may be the same as or different from each other. The number of substitutions of the alkyl group by the linear alkylene group is preferably one or two.

In the compound represented by Formula (A), structural isomers in which one or more positions of substitution of the alkyl group by the linear alkylene group are different may be present in the branched alkylene group. The compound represented by Formula (A) is also preferably a mixture of such structural isomers. The reason for this is because stability after long-term storage of the curable composition containing the compound represented by Formula (A) becomes higher. For example, in a case of a mixture of two kinds of structural isomers, it is sufficient for a mass ratio of the two kinds of structural isomers to be 10:90 to 90:10, and it is preferably 20:80 to 80:20.

Examples of divalent linking groups represented by each of R11 and R12 include a linking group containing a branched alkylene group in which one or more alkyl groups are substituted on a linear alkylene group; a linking group composed of one or more of the above-mentioned branched alkylene groups, and at least one selected from the group consisting of a linear alkylene group, an ether bond, an ester bond, a thioether bond, a thioester bond, an amide bond, and a carbonate bond; and the like. Among them, a linking group in which the branched alkylene groups, and the branched alkylene group and the linear alkylene group are linked via a linking group containing at least one selected from an ether bond, an ester bond, or a carbonate bond is preferable; and a linking group in which the branched alkylene groups, and the branched alkylene group and the linear alkylene group are linked via an ether bond or an ester bond is more preferable.

$R^{21}$ and $R^{22}$ each independently represent a hydrogen atom or a methyl group, and represent preferably a hydrogen atom.

In a case where $Ar^{11}$ and $Ar^{12}$ each independently are a fused ring group containing an aromatic ring surrounded by a broken line as one of rings constituting a fused ring, a group having $L^1$ as a linking group and a group having $L^2$ as a linking group each independently may be substituted on the aromatic ring surrounded by the broken line, or may be substituted on another ring constituting the fused ring than the aromatic ring surrounded by the broken line, but they each independently are preferably substituted on another ring constituting the fused ring than the aromatic ring surrounded by the broken line. In addition, in a case where $Ar^{13}$ and $Ar^1$ each independently are a fused ring group containing an aromatic ring surrounded by a broken line as one of rings constituting a fused ring, $R^3$ to $R^6$ each independently may be substituted on the aromatic ring surrounded by the broken line, or may be substituted on another ring constituting the fused ring than the aromatic ring surrounded by the broken line, but they each independently are preferably substituted on another ring constituting the fused ring than the aromatic ring surrounded by the broken line.

q and r each independently are preferably an integer of 0 to 2. As described above, except for a case where $L^1$ and $L^2$ are an ester bond, q and r are both preferably 0. v is preferably an integer of 0 to 2, and is more preferably 0. w is preferably an integer of 0 to 2, and is more preferably 0.

A molecular weight (weight-average molecular weight) of the compound represented by General Formula (A) is preferably 2,000 or less, is more preferably 1,500 or less, is even more preferably 1,000 or less, and is particularly preferably less than 1,000.

Specific examples of respective partial structures in a case where the compound represented by General Formula (A) is divided into partial structures A to D as follows, and specific examples of compounds represented by General Formula (A) as a combination of the respective partial structures are shown below. However, the compound represented by General Formula (A) and the respective partial structures are not limited to the following examples. The letter "Me" in the following structural formulas represents a methyl group.

General Formula (A)

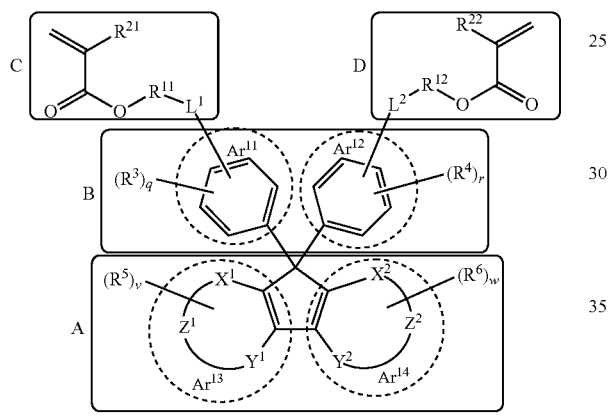

Specific Examples of Partial Structure A

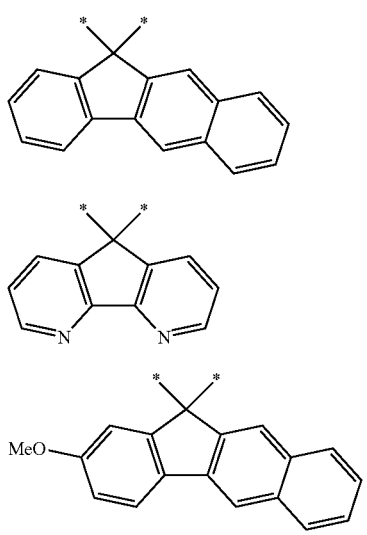

(A-1)

(A-2)

(A-3)

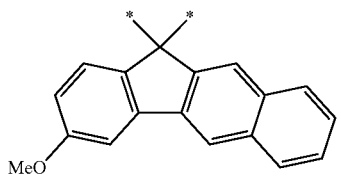

(A-4)

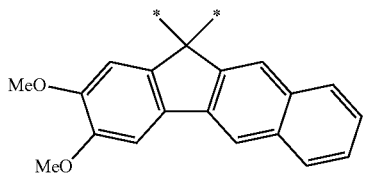

(A-5)

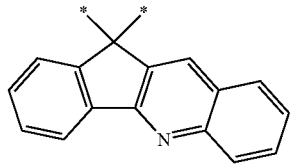

(A-6)

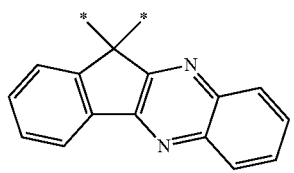

(A-7)

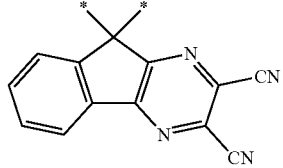

(A-8)

The symbol * indicates a bonding position with the partial structure B. Among them, A-1, A-3, A-4, A-5, A-6, and A-7 are preferable, A-1, A-5, and A-7 are more preferable, and A-5 and A-7 are particularly preferable.

Specific Examples of Partial Structure B

Hereinafter, a structure in which any two combinations selected from the group consisting of B-1, B-2, B-3, B-4, and B-5 are used as $Ar^{11}$ and $Ar^{12}$ will be exemplified.

(B-1)

(B-2)

(B-3)

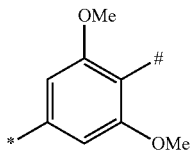
(B-4)

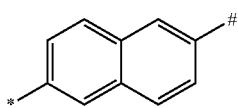
(B-5)

The symbol * indicates a bonding position with the partial structure A, and the symbol # indicates a bonding position with the partial structure C or D.

It is preferable that both $Ar^{11}$ and $Ar^{12}$ be B-1, both $Ar^{11}$ and $Ar^{12}$ be B-2, both $Ar^{11}$ and $Ar^{12}$ be B-3, or both $Ar^{11}$ and $Ar^{12}$ be B-4, and it is more preferable that both $Ar^{11}$ and $Ar^{12}$ be B-1, both $Ar^{11}$ and $Ar^{12}$ be B-2, or both $Ar^{11}$ and $Ar^{12}$ be B-3.

Specific Examples of Partial Structures C and D

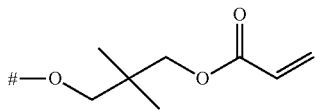
(C-1)

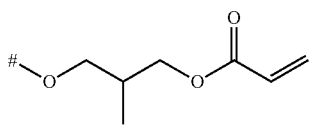
(C-2)

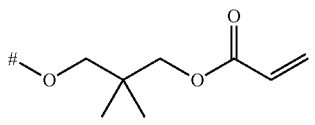
(C-3)

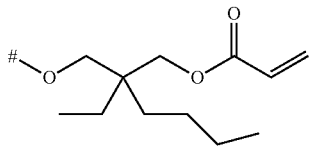
(C-4)

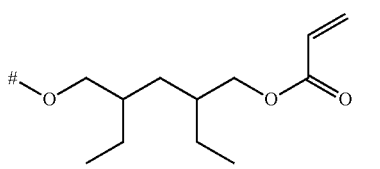
(C-5)

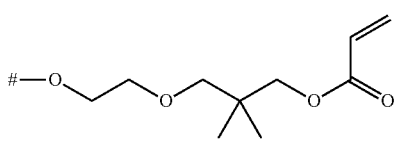
(C-6)

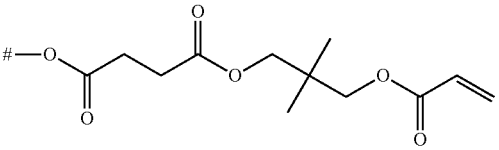
(C-7)

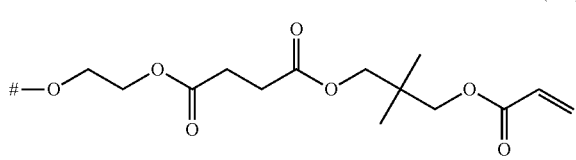
(C-8)

The following structure shows mixture of two partial structures of which methyl groups are respectively bonded to any one carbon of an ethylene group.

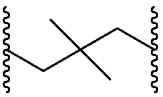 [SMILES: *CC(C)(C)C*]

In addition, the symbol # indicates a bonding position with the partial structure B.

Among the above structures, the partial structure C-1, C-7, or C-8 is preferable. The reason for this is because the compound represented by General Formula (A) becomes a mixture of structural isomers by the partial structure C-1, C-7, or C-8, and a content of the compound represented by General Formula (A) in a curable composition can then be made larger. In addition, stability after long-term storage can be improved.

Table 1 shows the specific examples of the compounds represented by General Formula (A) as a combination of the respective partial structures.

TABLE 1

|  | Partial structure A | Partial structure B | Partial structure C | Partial structure D |
|---|---|---|---|---|
| Compound (1) | A-1 | B-1(×2) | C-1 | C-1 |
| Compound (2) | A-2 | B-1(×2) | C-1 | C-1 |
| Compound (3) | A-3 | B-1(×2) | C-1 | C-1 |
| Compound (4) | A-4 | B-1(×2) | C-1 | C-1 |
| Compound (5) | A-5 | B-1(×2) | C-1 | C-1 |
| Compound (6) | A-6 | B-1(×2) | C-1 | C-1 |
| Compound (7) | A-7 | B-1(×2) | C-1 | C-1 |
| Compound (8) | A-8 | B-1(×2) | C-1 | C-1 |
| Compound (9) | A-1 | B-1(×2) | C-2 | C-2 |
| Compound (10) | A-1 | B-1(×2) | C-3 | C-3 |
| Compound (11) | A-1 | B-1(×2) | C-4 | C-4 |
| Compound (12) | A-1 | B-1(×2) | C-5 | C-5 |
| Compound (13) | A-1 | B-1(×2) | C-6 | C-6 |
| Compound (14) | A-1 | B-1(×2) | C-7 | C-7 |
| Compound (15) | A-5 | B-1(×2) | C-2 | C-2 |
| Compound (16) | A-5 | B-1(×2) | C-3 | C-3 |
| Compound (17) | A-5 | B-1(×2) | C-4 | C-4 |
| Compound (18) | A-5 | B-1(×2) | C-5 | C-5 |
| Compound (19) | A-5 | B-1(×2) | C-6 | C-6 |
| Compound (20) | A-5 | B-1(×2) | C-7 | C-7 |
| Compound (21) | A-7 | B-1(×2) | C-2 | C-2 |
| Compound (22) | A-7 | B-1(×2) | C-3 | C-3 |
| Compound (23) | A-7 | B-1(×2) | C-4 | C-4 |
| Compound (24) | A-7 | B-1(×2) | C-5 | C-5 |
| Compound (25) | A-7 | B-1(×2) | C-6 | C-6 |
| Compound (26) | A-7 | B-1(×2) | C-7 | C-7 |

TABLE 1-continued

|  | Partial structure A | Partial structure B | Partial structure C | Partial structure D |
|---|---|---|---|---|
| Compound (27) | A-7 | B-3(×2) | C-2 | C-2 |
| Compound (28) | A-7 | B-3(×2) | C-6 | C-6 |
| Compound (29) | A-7 | B-3(×2) | C-7 | C-7 |
| Compound (30) | A-1 | B-2(×2) | C-7 | C-7 |
| Compound (31) | A-1 | B-3(×2) | C-7 | C-7 |
| Compound (32) | A-1 | B-4(×2) | C-7 | C-7 |
| Compound (33) | A-1 | B-5(×2) | C-7 | C-7 |
| Compound (34) | A-7 | B-3(×2) | C-2 | C-3 |
| Compound (35) | A-7 | B-3(×2) | C-2 | C-7 |
| Compound (36) | A-7 | B-1(×2) | C-8 | C-8 |

The compound represented by Formula (A) has one or two or more asymmetric carbons in some cases, and regarding stereochemistry of such asymmetric carbons, compounds represented by Formula (A) each independently can be any of an (R) isomer or an (S) isomer. In addition, the compound represented by Formula (A) may be a mixture of stereoisomers such as optical isomers or diastereoisomers. In other words, the compound represented by Formula (A) may be any kind of stereoisomer, may be any mixture of stereoisomers, or may be a racemate.

(Curable Composition)

The curable composition contains at least the compound represented by General Formula (A). In addition to the compound represented by General Formula (A), the curable composition may include other components such as a polymerization initiator, a (meth)acrylate monomer other than the compound represented by General Formula (A), and a non-conjugated-vinylidene-group-containing compound.

By using the curable composition of the embodiment of the present invention which contains at least the compound represented by General Formula (A), it is possible to obtain a cured product having a small Abbe number. An Abbe number of a cured product formed from the curable composition of the embodiment of the present invention is not particularly limited, but an Abbe number of the cured product is preferably 30 or less, is more preferably 25 or less, is even more preferably 23 or less, and is particularly preferably 21 or less.

An Abbe number (vd) of the cured product formed from the curable composition is a value measured using a Kalnew precision refractometer KPR-2000 (manufactured by Shimadzu Device Corporation). Specifically, the curable composition is poured into a transparent glass mold having a diameter of 20 mm and a thickness of 2 mm, and heated at 200° C. in an atmosphere having an oxygen concentration of 1% or less to form a cured product (a heating step), and an Abbe number (vd) of this cured product is measured. The Abbe number (vd) of the cured product is calculated by the following formula. In a case of molding a cured product, an ultraviolet irradiation step may be employed instead of the above-described heating step, or both of the heating step and the ultraviolet irradiation step may be employed.

$$vd=(nd-1)/(nF-nC)$$

Where, nd represents a refractive index at a wavelength of 587.56 nm, nF represents a refractive index at a wavelength of 486.13 nm, and nC represents a refractive index at a wavelength of 656.27 nm.

A viscosity of the curable composition of the embodiment of the present invention is preferably 20,000 mPa·s or less, is more preferably 15,000 mPa·s or less, is even more preferably 13,000 mPa·s or less, and is particularly preferably 10,000 mPa·s or less. By setting the viscosity of the curable composition within the above range, it is possible to improve handleability in a case of molding a cured product, thereby forming a high-quality cured product. A viscosity of the curable composition is preferably 2,000 mPa·s or more, is more preferably 3,000 mPa·s or more, is even more preferably 4,000 mPa·s or more, and is particularly preferably 5,000 mPa·s or more.

The content of the compound represented by General Formula (A) in the curable composition is preferably 10% to 90% by mass, is more preferably 20% to 85% by mass, and is even more preferably 30% to 80% by mass with respect to the total mass of the curable composition. By setting the content of the compound represented by General Formula (A) within the above range, it is possible to obtain a cured product which has excellent handleability in a case of molding a cured product and has a small Abbe number.

Two or more compounds represented by General Formula (A) may be contained in the curable composition. In a case where two or more compounds represented by General Formula (A) are contained, the total content thereof is preferably within the above range.

<(Meth)Acrylate Monomer>

The curable composition may contain a (meth)acrylate monomer other than the compound represented by General Formula (A). The (meth)acrylate monomer may be a polyfunctional (meth)acrylate monomer having two or more (meth)acryloyl groups in a molecule, or may be a monofunctional (meth)acrylate monomer having one (meth)acryloyl group in a molecule. The (meth)acrylate monomer can be added for improving compatibility of the entire system, adjusting a viscosity, and adjusting physical properties (for example, a glass transition temperature) of a cured product.

Specific examples of (meth)acrylate monomers include a (meth)acrylate monomer described in paragraphs 0037 to 0046 of JP2012-107191A.

Examples of (meth)acrylate monomers that can be preferably used in the present invention include a monofunctional (meth)acrylate monomer having an aromatic ring such as the following monomer 1 (phenoxyethyl acrylate) or monomer 2 (benzyl acrylate), a monofunctional (meth) acrylate monomer having an aliphatic ring such as the following monomer 3 (tricyclodecane dimethanol diacrylate) or monomer 4 (dicyclopentanyl acrylate), and the following monomer 5 (allyl methacrylate). A molecular weight of the (meth)acrylate monomer is preferably 100 to 500.

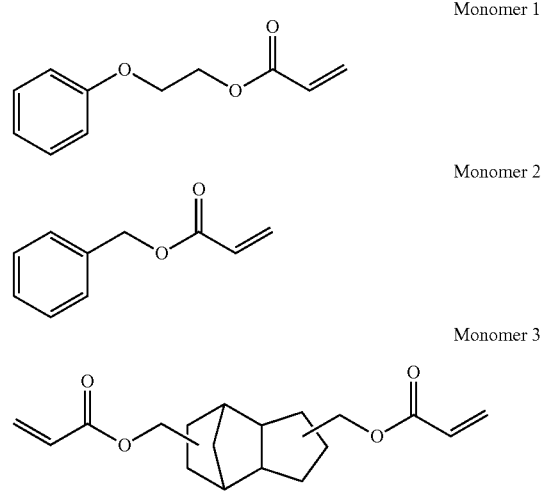

-continued

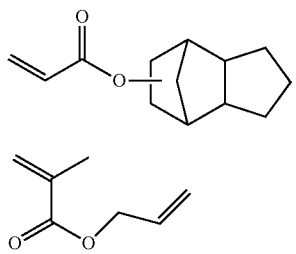

Monomer 4

Monomer 5

The method of obtaining the (meth)acrylate monomer is not particularly limited, and the compound may be commercially available or may be manufactured by synthesis. In a case of commercially obtaining the compound, for example, VISCOAT #192 PEA (Monomer 1) (manufactured by Osaka Organic Chemical Industry Ltd.), VISCOAT #160 BZA (Monomer 2) (manufactured by Osaka Organic Chemical Industry Ltd.), A-DCP (Monomer 3) (manufactured by Shin-Nakamura Chemical Co., Ltd.), or FA-513AS (Monomer 4) (manufactured by Hitachi Chemical Co., Ltd.) may be preferably used.

When the curable composition of the embodiment of the present invention contains a (meth)acrylate monomer, the content of the (meth)acrylate monomer is preferably 1% to 80% by mass, more preferably 2% to 50% by mass, and even more preferably 3% to 45% by mass, with respect to the total mass of the curable composition.

<Polymer Having Radically Polymerizable Group in Side Chain>

The curable composition may further contain a polymer having a radically polymerizable group in a side chain, in addition to the above-described compound. Because the polymer having a radically polymerizable group in a side chain functions to increase a viscosity of the curable composition, it can also be called a thickener or a thickening polymer. The polymer having a radically polymerizable group in a side chain can be added for adjusting a viscosity of the curable composition.

The polymer having a radically polymerizable group in the side chain may be a homopolymer or a copolymer. Among them, it is preferable that the polymer which has a radically polymerizable group in a side chain be a copolymer. When the polymer having a radically polymerizable group in the side chain is a copolymer, it is sufficient that at least one copolymer component has a radically polymerizable group. In addition, in a case where the polymer having a radically polymerizable group in the side chain is a copolymer, the thickening polymer is more preferably a copolymer containing a monomer unit having a radically polymerizable group in the side chain and a monomer unit having an aryl group in the side chain.

Examples of radically polymerizable groups include a (meth)acrylate group, a vinyl group, a styryl group, and an allyl group. The polymer having a radically polymerizable group in the side chain preferably contains 5% to 100% by mass, more preferably 10% to 90% by mass, and even more preferably 20% to 80% by mass of repeating units having a radically polymerizable group.

In the following, specific examples of the polymer having a radically polymerizable group in the side chain preferably used in the present invention are exemplified, but the polymer having a radically polymerizable group in the side chain is not limited to the following structure. Each of the specific examples shown below is a copolymer, and each copolymer includes two or three structural units illustrated adjacent thereto. For example, the specific example described at the top is an allyl methacrylate-benzyl methacrylate copolymer.

In the structural formulas below, Ra and Rb each independently represent hydrogen or a methyl group. Note that a plurality of Ra's in one polymer may be the same or different. n represents an integer of 0 to 10, preferably 0 to 2, and more preferably 0 or 1.

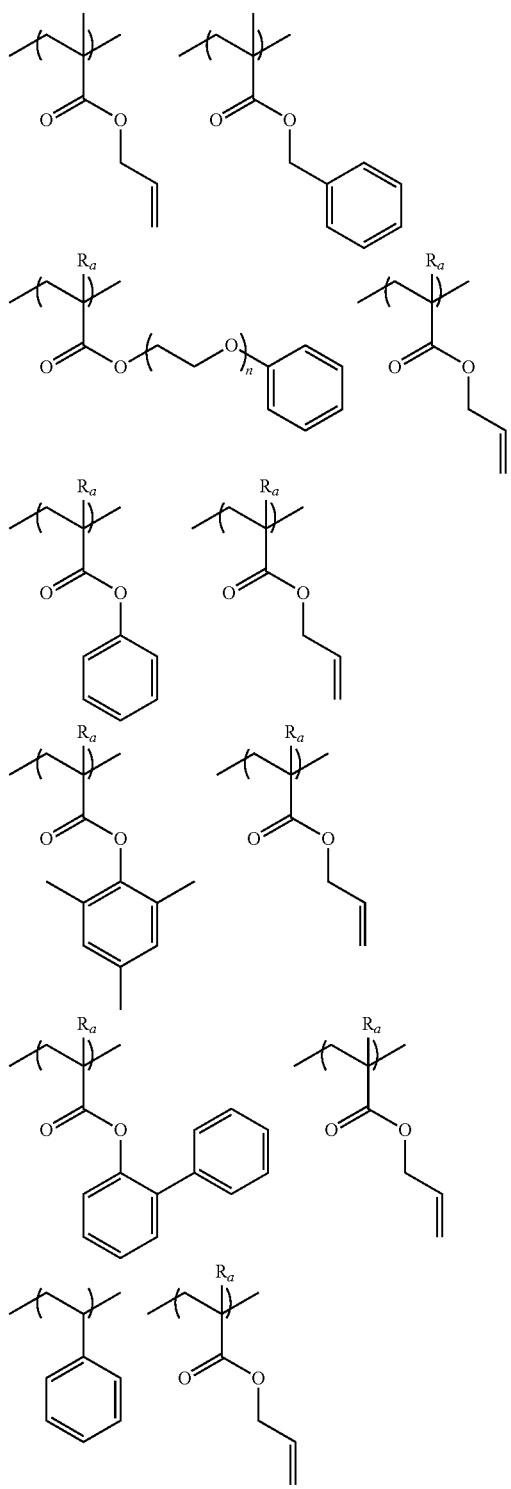

-continued
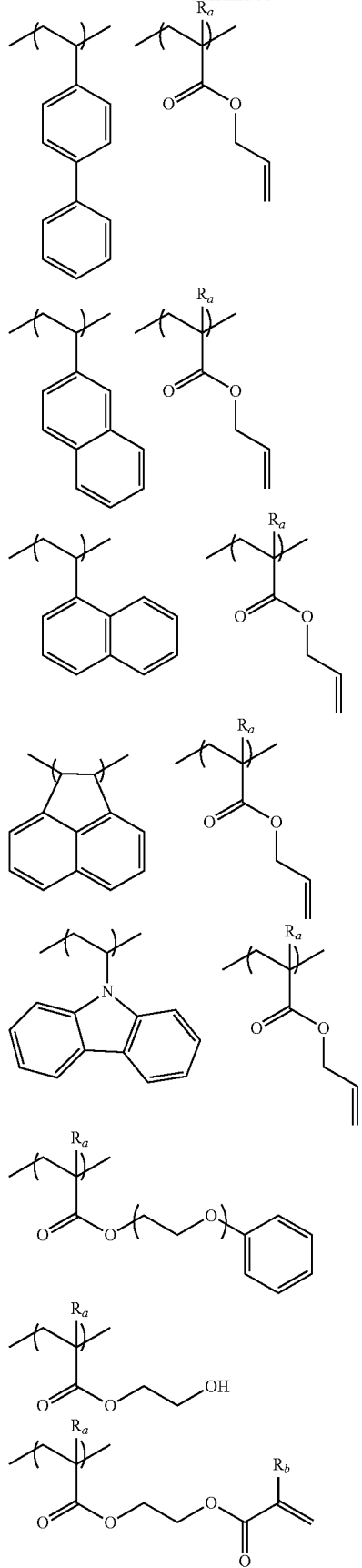
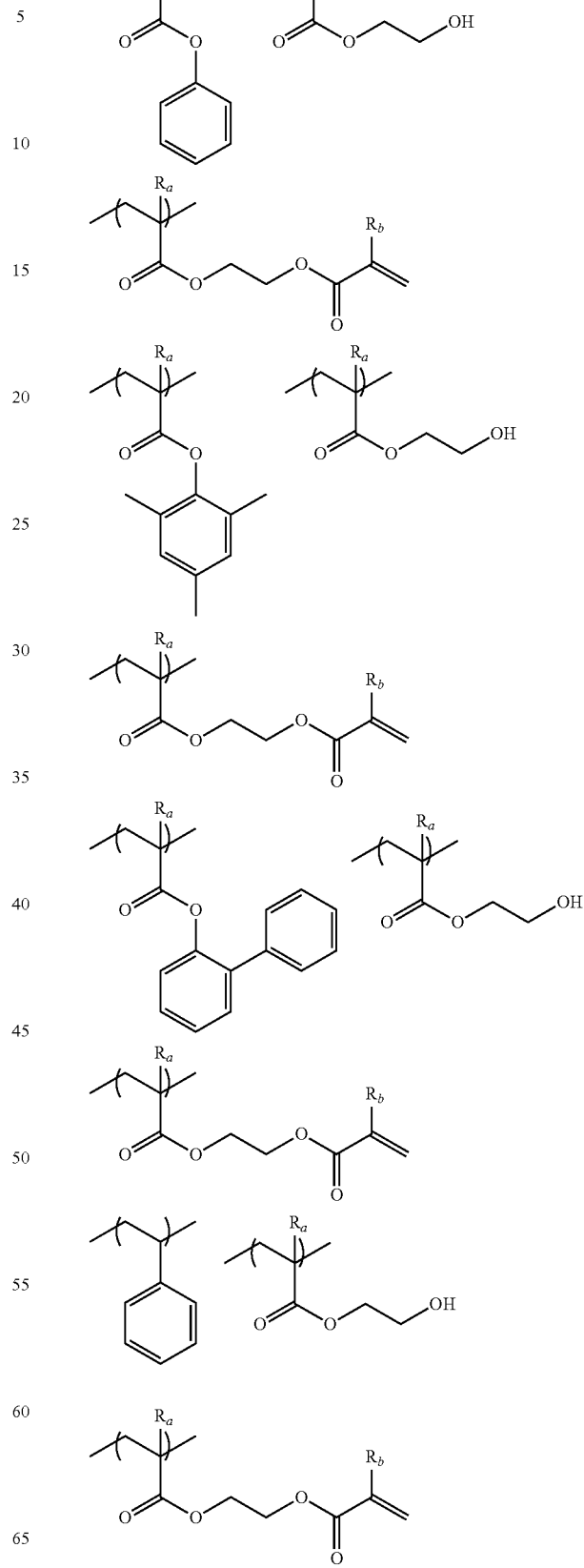

-continued
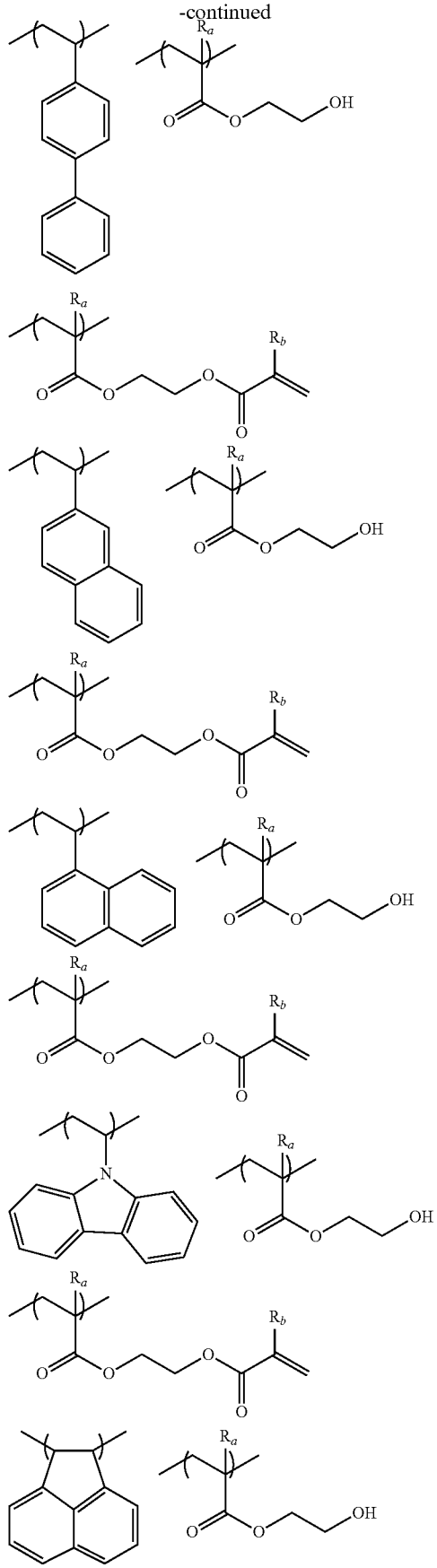
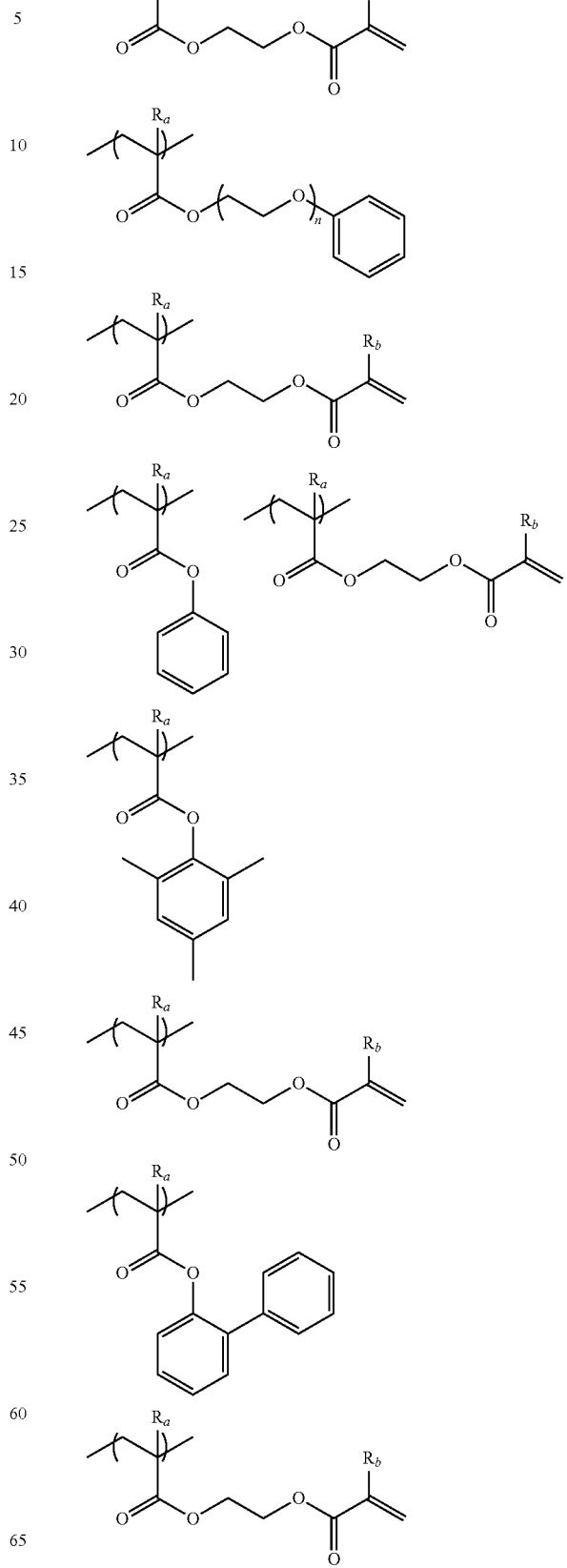

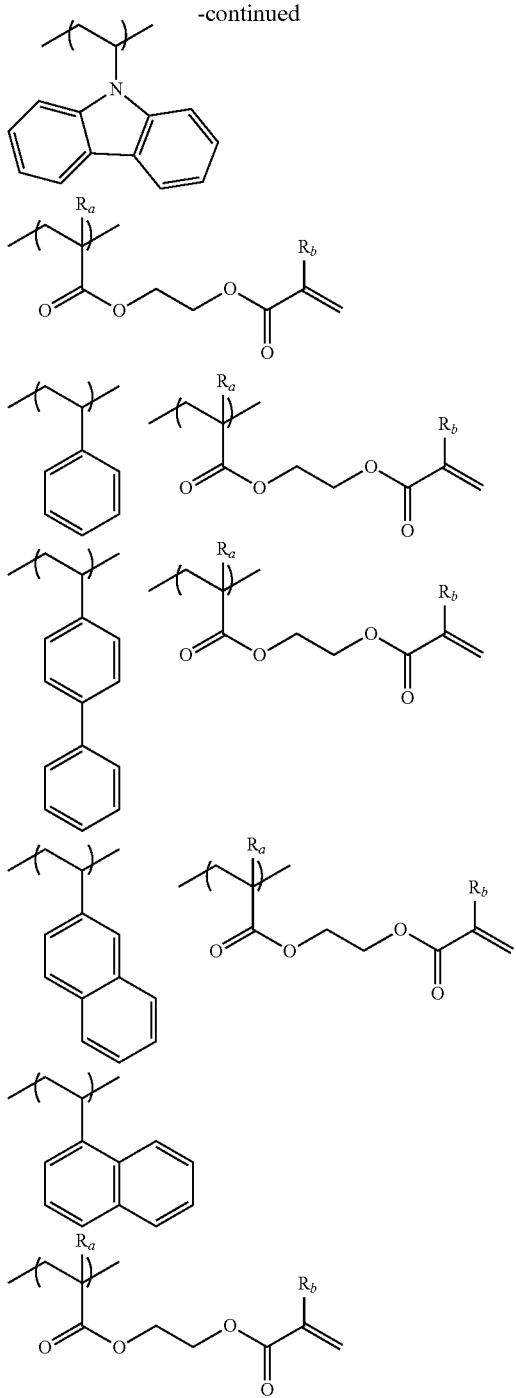

The molecular weight (weight-average molecular weight) of the polymer having a radically polymerizable group in the side chain is preferably 1,000 to 10,000,000, more preferably 5,000 to 300,000, and even more preferably 10,000 to 200,000. The glass transition temperature of the polymer having a radically polymerizable group in the side chain is preferably 50° C. to 400° C., more preferably 70° C. to 350° C., and even more preferably 100° C. to 300° C.

The content of the polymer having a radically polymerizable group in the side chain is preferably 40% by mass or less, more preferably 30% by mass or less, and even more preferably 25% by mass or less with respect to the total mass of the curable composition. The content of the polymer having a radically polymerizable group in the side chain may be 0% by mass, and an aspect in which a polymer having a radically polymerizable group in the side chain is not added is also preferable.

<Non-Conjugated-Vinylidene-Group-Containing Compound>

The curable composition according to the embodiment of the present invention may contain a non-conjugated-vinylidene-group-containing compound. By adding the non-conjugated-vinylidene-group-containing compound, it is possible to control a viscosity of a semi-cured product obtained by subjecting the curable composition to photoirradiation or heating the curable composition to a specific range, and to improve heat resistance and non-defective product rate of a cured product obtained by thermally polymerizing this semi-cured product in a method for manufacturing a cured product of the embodiment of the present invention to be described later.

As the non-conjugated-vinylidene-group-containing compound, it is possible to use a compound described in paragraphs 0016 to 0033 of JP2012-107191A. The present specification incorporates the contents described in paragraphs 0016 to 0033 of JP2012-107191A.

The molecular weight of the non-conjugated-vinylidene-group-containing compound is preferably 100 to 400, more preferably 120 to 350, and particularly preferably 130 to 300.

The method of obtaining the non-conjugated-vinylidene-group-containing compound is not particularly limited, and the compound may be commercially available or may be manufactured by synthesis. In a case of commercially obtaining the compound, for example, i-caryophyllene (manufactured by Inoue Perfumery Co., Ltd.) and (+)-limonene (manufactured by Tokyo Chemical Industry Co., Ltd.) can be preferably used.

When the curable composition of the embodiment of the present invention contains a non-conjugated-vinylidene-group-containing compound, a content of the non-conjugated-vinylidene-group-containing compound is preferably 0.5% to 30% by mass, more preferably 1% to 25% by mass, and even more preferably 2% to 20% by mass, with respect to the total mass of the curable composition.

(Polymerization Initiator)

The curable composition according to the embodiment of the present invention contains at least one selected from a photoradical polymerization initiator or a thermal radical polymerization initiator.

<Thermal Radical Polymerization Initiator>

The curable composition preferably contains a thermal radical polymerization initiator. By this action, it is possible to mold a cured product having high heat resistance by thermally polymerizing the curable composition.

Specifically, the following compounds can be used as the thermal radical polymerization initiator. Examples of the thermal radical polymerization initiator include 1,1-di(t-hexylperoxy)cyclohexane, 1,1-di(t-butylperoxy)cyclohexane, 2,2-di(4,4-di-(t-butylperoxy)cyclohexyl)propane, t-hexylperoxyisopropyl monocarbonate, t-butylperoxy-3,5,5-trimethylhexanoate, t-butylperoxy laurate, dicumyl peroxide, di-t-butyl peroxide, t-butylperoxy-2-ethylhexanoate, t-hexylperoxy-2-ethylhexanoate, cumene hydroperoxide, t-butyl hydroperoxide, t-butylperoxy-2-ethylhexyl, 2,3-dimethyl-2,3-diphenylbutane, and the like.

Among them, it is preferable that the curable composition of the embodiment of the present invention contains a hydroperoxide compound as a thermal radical polymerization initiator. The hydroperoxide compound is a peroxide and a compound having a peroxy group. In the hydroperoxide compound, one oxygen atom of the peroxy group (—O—O—) is substituted by a hydrogen atom and includes a hydroperoxide group (—O—O—H). Hydroperoxide compounds having hydroperoxide groups in the molecule have the effect of promoting chain transfer during the polymerization of non-conjugated-vinylidene-group-containing compounds, and the controllability of the three-dimensional structure when the curable composition is cured is more improved, and thereby it is possible to improve and impart deformability to the semi-cured product.

The method of obtaining the hydroperoxide compound is not particularly limited, and the compound may be commercially available or may be manufactured by synthesis. When commercially obtained, for example, PERCUMYL H-80 (cumene hydroperoxide) manufactured by Nippon Oil & Fats Co., Ltd. can be used.

The thermal radical polymerization initiator preferably includes a hydroperoxide compound and another thermal radical polymerization initiator. Examples of other thermal radical polymerization initiators include non-hydroperoxide compounds. Since the hydroperoxide compound generally has a high temperature for initiating thermal radical polymerization, it preferably contains both non-hydroperoxide compounds having a low thermal polymerization initiation temperature. As non-hydroperoxide compounds, it is preferable to use a peroxyester compound such as t-butylperoxy-2-ethylhexanoate (Perbutyl O, manufactured by Nippon Yushi Co., Ltd.), and t-butylperoxy-2-ethylhexyl carbonate (Perbutyl E, manufactured by Nippon Yushi Co., Ltd.).

The content of the thermal radical polymerization initiator is preferably 0.01% to 10% by mass, more preferably 0.05% to 5.0% by mass, and even more preferably 0.05% to 2.0% by mass, with respect to the total mass of the curable composition.

<Photoradical Polymerization Initiator>

The curable composition preferably contains a photoradical polymerization initiator. Specifically, the following compounds can be used as the photoradical polymerization initiator. Examples of the photoradical polymerization initiator include bis(2,6-dimethoxybenzoyl)-2,4,4-trimethylpentylphosphine oxide, bis(2,6-dimethylbenzoyl)-2,4,4-trimethylpentylphosphine oxide, bis(2,4,6-trimethylbenzoyl)-2,4,4-trimethylpentylphosphine oxide, bis(2,6-dichlorobenzoyl)-2,4,4-trimethylpentylphosphine oxide, 1-phenyl-2-hydroxy-2-methylpropan-1-one, 1-hydroxycyclohexyl phenyl ketone, 1-(4-isopropylphenyl)-2-hydroxy-2-methylpropan-1-one, 1,2-diphenylethanedione, methylphenyl glyoxylate, 1-[4-(2-hydroxyethoxy)-phenyl]-2-hydroxy-2-methyl-1-propan-1-one, 2-hydroxy-1-{4-[4-(2-hydroxy-2-methyl-propionyl)-benzyl]phenyl}-2-methyl-propan-1-one, 2,2-dimethoxy-1,2-diphenylethan-1-one, 2-methyl-1-(4-methylthiophenyl)-2-morpholinopropan-1-one, 2-benzyl-2-dimethylamino-1-(4-morpholinophenyl)butanone-1,2,4,6-trimethylbenzoyl-diphenyl-phosphine oxide, and bis(2,4,6-trimethylbenzoyl)-phenylphosphine oxide.

Of the above, in the present invention, BASF's IRGACURE 184 (1-hydroxycyclohexyl phenyl ketone), IRGACURE 819 (bis(2,4,6-trimethylbenzoyl)-phenylphosphine oxide), IRGACURE 651 (2,2-dimethoxy-1,2-diphenylethane-1-one), 1-[4-(2-hydroxyethoxy)-phenyl]-2-hydroxy-2-methyl-1-propan-1-one, or 2-methyl-1-(4-methylthiophenyl)-2-morpholinopropan-1-one may be preferably used as the photoradical polymerization initiator.

The content of the photoradical polymerization initiator is preferably 0.01% to 5.0% by mass, more preferably 0.05% to 1.0% by mass, and even more preferably 0.05% to 0.5% by mass, with respect to the total mass of the curable composition.

The curable composition preferably contains both a photoradical polymerization initiator and a thermal radical polymerization initiator described above, and in this case, the total content of a photoradical polymerization initiator and a thermal radical polymerization initiator is preferably 0.01% to 10% by mass, more preferably 0.05% to 5.0% by mass, and even more preferably 0.05% to 3.0% by mass, with respect to the total mass of the curable composition.

<Other Additives>

Unless contrary to the gist of the present invention, the curable composition may contain additives such as a polymer, a monomer, a dispersant, a plasticizer, a thermal stabilizer, or a mold release agent other than the components described above. For example, JP-506H manufactured by Johoku Chemical Co., Ltd. can be used as a mold release agent.

(Method for Producing Cured Product)

The method for manufacturing a cured product includes a step of photocuring the above-described curable composition and/or a step of thermosetting. Among them, a method for manufacturing a cured product preferably includes a step of forming a semi-cured product by irradiating the curable composition with light or heating the curable composition; and a step of forming a cured product by irradiating the obtained semi-cured product with light or heating the obtained semi-cured product.

<Step of Forming Semi-Cured Product>

The step of forming a semi-cured product preferably includes a transfer step. A transfer step is a step of pressing a mold against the curable composition mentioned above. In the transfer step, the other mold is pressed against the curable composition injected into one of the pair of molds to spread the curable composition.

It is preferable that the mold used with the manufacturing method of cured products is a mold subjected to a chromium nitride treatment. Thereby, a favorable mold releasability can be obtained in a release step to be performed the subsequent steps, and the manufacture efficiency of the optical member can be increased.

Examples of chromium nitride treatment include a method of forming a chromium nitride film on the mold surface. Examples of methods for forming a chromium nitride film on the mold surface include a Chemical Vapor Deposition (CVD) method and a Physical Vapor Deposition (PVD) method. The CVD method is a method of forming a chromium nitride film on a substrate surface by reacting a source gas containing chromium and a source gas containing nitrogen at a high temperature. The PVD method is a method of forming a chromium nitride film on the surface of the substrate using an arc discharge (arc type vacuum deposition method). In this arc type vacuum deposition method, a cathode (evaporation source) made of chromium, for example, is placed in the vacuum vessel, an arc discharge is caused between the cathode and the wall of the vacuum vessel via a trigger, ionization of the metal by arc plasma is performed at the same time as vaporizing the cathode, a negative voltage is applied to the substrate, and about several tens of mTorr (1.33 Pa) of a reaction gas (for example, a nitrogen gas) is put into the vacuum vessel, and thereby the ionized metal and the reaction gas are reacted on the surface of the substrate to form a compound film. In the present invention, the chromium nitride treatment on the mold surface is performed by the CVD method or the PVD method.

In general, the mold can be heated while pressing the contents by combining two molds. In a case where a low viscosity composition is injected into the mold, leakage into the mold clearance is caused. For this reason, it is preferable that the curable composition inject into a mold has a certain viscosity or more. In order to adjust the viscosity of the curable composition, a polymer having the above-described radically polymerizable group in the side chain may be added to the curable composition.

After the step of pressing the mold, a step of forming a semi-cured product is performed. The semi-cured product can be obtained by semi-curing the curable composition injected into the mold. In the step of forming the semi-cured product, photoirradiation or heating is performed. In the present specification, such a step can also be called a semi-curing step.

In the step of molding a semi-cured product, the curable composition according to the embodiment of the present invention is subjected to at least one of photoirradiation or heating. In semi-curing, there is generally no difference in Abbe number of a finally obtained cured product, regardless of whether photoirradiation is performed or heating is performed. In the step of semi-curing, it is preferable to form a semi-cured product having a complex viscosity of $10^5$ to $10^8$ mPa·s at 25° C. and a frequency of 10 Hz.

The term "semi-cured product" in the present specification refers to a product obtained by polymerizing a curable composition, which is not completely solid and has fluidity to some extent. A polymer of a curable composition in such a state that its complex viscosity at 25° C. and at a frequency of 10 Hz is $10^5$ to $10^8$ mPa·s is a semi-cured product. That is, those of which the upper limit value of the complex viscosity at 25° C. and at a frequency of 10 Hz is less than $1.0 \times 10^9$ mPa·s are considered to fall within a range of semi-cured products. On the other hand, the term "cured product" refers to a product produced by curing a curable composition by polymerization and is in a state of being completely solid.

The light used in the photoirradiation is preferably ultraviolet light or visible light and more preferably ultraviolet light. For example, a metal halide lamp, a low pressure mercury lamp, a high pressure mercury lamp, an ultrahigh pressure mercury lamp, a germicidal lamp, a xenon lamp, a light emitting diode (LED) light source lamp, or the like is suitably used. The atmosphere during photoirradiation is preferably air or an inert gas purged atmosphere and is more preferably an atmosphere purged with nitrogen until an oxygen concentration becomes 1% or less.

In a case of providing a heating and semi-curing step in the semi-curing step, the semi-curing by heating is carried out so that the complex viscosity of the semi-cured product at 25° C. and at a frequency of 10 Hz after heating is preferably $10^5$ to $10^8$ mPa·s.

The present invention may relate to a semi-cured product manufactured by the above-described method. Such a semi-cured product may be preferably used for a method for manufacturing a cured product to be described later. The preferred range of the complex viscosity of the semi-cured product is the same as the preferred range of the complex viscosity of the semi-cured product in the above-described step of forming a semi-cured product.

The semi-cured product may not contain the photoradical polymerization initiator at all after the photoirradiation step, since the initiator is completely consumed in the step, or the photoradical polymerization initiator may remain in the semi-cured product.

In addition, the glass transition temperature of the semi-cured product is preferably −150° C. to 0° C., more preferably −50° C. to 0° C., and particularly preferably −20° C. to 0° C.

<Step of Forming Cured Product>

The step of forming a cured product preferably includes a polymerization step of obtaining a cured product by thermal polymerization in which the semi-cured product is inserted into a molding mold for pressure deformation therein and is heated therein, or by photopolymerization in which photoirradiation is performed. In the present specification, such a step can also be called a curing step. The photoirradiation conditions and the heating conditions in the forming step of a cured product are the same as those in the semi-curing step described above.

In a case where the curing step is a thermal polymerization step, the molding mold used in the polymerization step is also referred to as a thermoforming mold. In general, the thermoforming mold is composed of two molding mold parts and is preferably designed so that contents can be heated under pressure in the combination of the two molding mold parts. In the method for producing a cured product, a metallic mold is more preferably used as the molding mold in the thermal polymerization step to obtain a cured product. The thermoforming mold of the type for use herein is described, for example, in JP2009-126011A. In addition, it is preferable that the mold is a mold subjected to a chromium nitride treatment.

In the thermal polymerization step, the semi-cured product put in a molding mold is deformed under pressure and heated for thermal polymerization to obtain a cured product. Here, pressure deforming and heating may be carried out simultaneously, or heating may be carried out after pressure deforming, or pressure deforming may be carried out after heating. Above all, preferably, pressure deforming and heating are carried out simultaneously. Also preferably, after simultaneous pressure deforming and heating, the product may be further heated at a higher temperature after the pressure applied thereto has become stable.

In the thermal polymerization step, the semi-cured product is heated and cured at a temperature of 150° C. or higher to obtain a cured product.

The heating temperature is 150° C. or higher, preferably 160° C. to 270° C., more preferably 165° C. to 250° C., and even more preferably 170° C. to 230° C.

In this curing step, it is preferable to perform heating and pressure deformation. Thereby, the inverted shape of the inner surface of the mold can be accurately transferred to the cured product.

The pressure for the pressure deforming is preferably 0.098 MPa to 9.8 MPa, more preferably 0.294 MPa to 4.9 MPa, and particularly preferably 0.294 MPa to 2.94 MPa.

The time of thermal polymerization is preferably 30 to 1,000 seconds, more preferably 30 to 500 seconds, and particularly preferably 60 to 300 seconds. The atmosphere during thermal polymerization is preferably air or an inert gas purged atmosphere and more preferably an atmosphere purged with nitrogen until an oxygen concentration becomes 1% or less.

A release step is provided after the curing step. When thermal polymerization is performed in the curing step, it is preferable that the mold is separated from the cured product in a temperature range of 150° C. to 250° C. in the mold release step. By setting the temperature in the mold release step within the above range, the mold can be easily separated from the cured product, and the manufacture efficiency can be increased.

As mentioned above, although an example of the manufacturing method of the cured product of the embodiment of the present invention was described, the structure of the present invention is not restricted thereto, and it can be suitably changed within the range which does not deviate from the present invention. For example, the mold used in the transfer step and the semi-curing step may be used as it is in the curing step; or after performing the semi-curing step, the mold may be pulled away from the semi-cured product, and the semi-cured product may be moved to another mold (thermoforming mold) to perform the curing step. In this case, it is preferable that the above-described chromium treatment is performed on the mold used in the semi-curing step and the curing step.

Furthermore, in the semi-curing step, the curable composition in the mold may be irradiated with light and heated. Thereby, the semi-cured product which has a desired degree of curing can be obtained reliably.

(Semi-Cured Product)

The semi-cured product can be formed by semi-curing the above-described curable composition. The semi-cured product is preferably a semi-cured product produced by the above-mentioned method for producing a semi-cured product. In addition, the semi-cured product preferably has a complex viscosity of $10^5$ to $10^8$ mPa·s and a frequency of 10 Hz at 25° C.

(Cured Product)

The present invention also relates to a cured product of a curable composition. The cured product can be formed by curing the above-described semi-cured product. The cured product according to the embodiment of the present invention is preferably a cured product produced by the above-mentioned method for producing a cured product.

(Size)

The maximum thickness of the cured product according to the embodiment of the present invention is preferably 0.1 to 10 mm. The maximum thickness is more preferably 0.1 to 5 mm and particularly preferably 0.15 to 3 mm. The cured product according to the embodiment of the present invention is preferably a circular shape with the maximum diameter of 1 to 1,000 mm. The maximum diameter is more preferably 2 to 200 mm and particularly preferably 2.5 to 100 mm.

(Optical Members)

The present invention also relates to an optical member including the above-mentioned cured product. Since the cured product according to the embodiment of the present invention is a molded body having excellent optical properties, it is preferably used as an optical member. The type of the optical member according to the embodiment of the present invention is not particularly limited. In particular, the cured product according to the embodiment of the present invention is suitably used for optical members that utilize the excellent optical properties of curable compositions, especially for light-transmissive optical members (so-called passive optical members). Examples of optically-functional devices equipped with such optical members include various types of display devices (a liquid crystal display, a plasma display, and the like), various types of projector devices (an overhead projector (OHP), a liquid crystal projector, and the like), optical fiber communication systems (a optical waveguide, a light amplifier, and the like), and image-taking devices such as a camera and a video.

Examples of the passive optical members for use in optically-functional devices include lenses, prisms, prism sheets, panels (plate-like molded bodies), films, optical waveguides (film-like optical waveguide, a fiber-like optical waveguide, and the like), optical discs, and LED sealants. If desired, the passive optical members may be provided with an optional coating layer, such as a protective layer for preventing mechanical damage of the coating surface by friction or abrasion, a light-absorbing layer for absorbing the light having an undesirable wavelength to cause degradation of inorganic particles, substrates and others, a blocking layer for suppressing or preventing permeation of reactive small molecules such as moisture or oxygen gas, an antiglare layer, an antireflection layer, a layer of low refractive index, or the like, as well as any additional functional layer. Specific examples of the optional coating layer include a transparent conductive film or gas barrier film formed of an inorganic oxide coating layer, and a gas barrier film or hard coating film formed of an organic coating layer. The coating method for forming the coating layer may be any known coating method such as a vacuum deposition method, a CVD method, a sputtering method, a dip coating method, or a spin coating method.

Application Examples

The optical member obtained from the cured product according to the embodiment of the present invention is especially preferable for a lens substrate. The lens substrate produced using the curable composition according to the embodiment of the present invention has a low Abbe number and preferably has high refractivity, high light transmittance and lightweightness and is excellent in optical properties. By suitably adjusting the type of monomer constituting the curable composition, it is possible to control the refractive index of the lens substrate in any desired manner.

In addition, in the present specification, the "lens substrate" refers to a single member capable of exhibiting a lens function. On and around the surface of the lens substrate, any film and member may be provided depending on the use environment and applications of lenses. For example, a protective film, an antireflection film, a hard coating film, or the like may be formed on the surface of the lens substrate. Further, it can be a compound lens in which a glass lens substrate or a plastic lens substrate is laminated. It is also possible to make the periphery of the lens substrate intrude and be fixed in a substrate holding frame or the like. However, those films and frames or the like are additional members to the lens substrate and therefore differ from the lens substrate itself referred to in the present specification.

In a case of using the lens substrate for lenses, the lens substrate itself may be used as a lens by itself, or additional films or frames or additional lens substrates may be added thereto for use as a lens, as mentioned above. The type and the shape of the lens formed of the lens substrate are not particularly limited.

The lens substrate is preferably used for, for example, lenses for imaging devices such as mobile phones or digital cameras; lenses for movie devices such as TV or video cameras; and lenses for in-vehicle devices or endoscope lenses.

EXAMPLES

Hereinafter, the features of the present invention will be more specifically described with reference to Examples and Comparative Examples. In the following Examples, the materials to be used, amounts and ratios thereof, the details of the treatment and the treatment procedures, and the like may be suitably modified or changed without departing from the scope of the present invention. Accordingly, the scope of the present invention should not be limitedly interpreted by the following specific Examples.

Synthesis Example
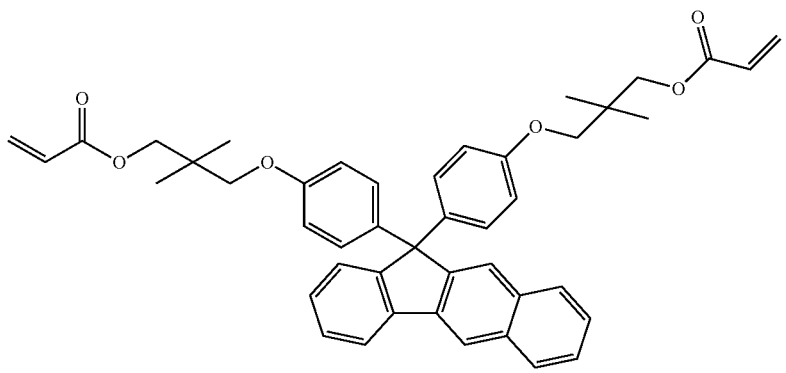
Compound 1
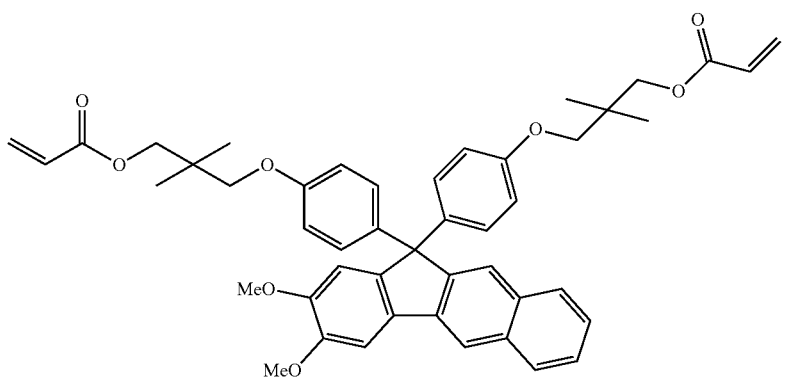
Compound 5
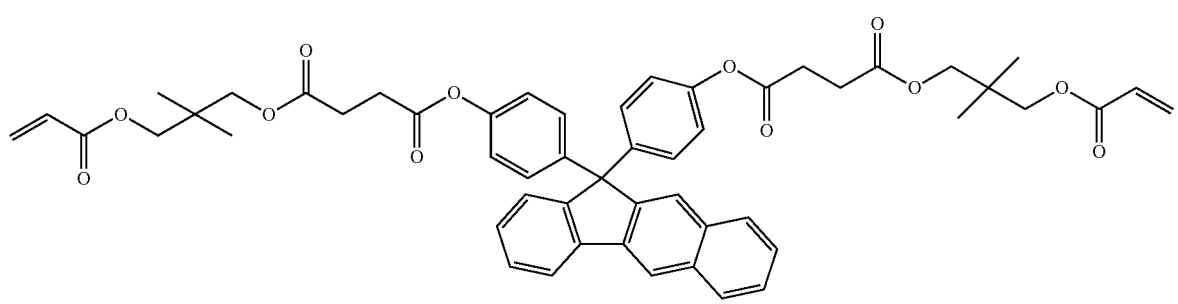
Compound 14
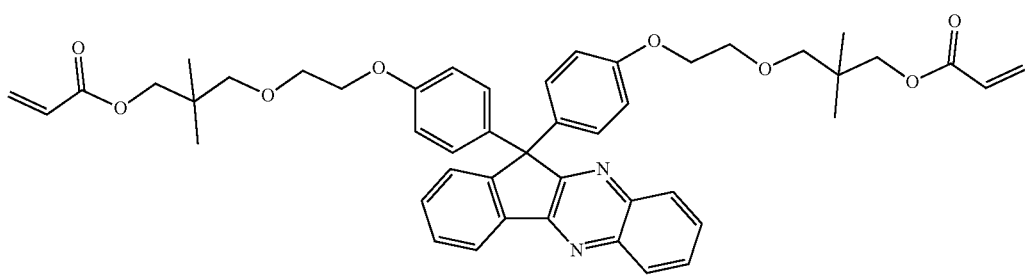
Compound 25

-continued
Compound 26
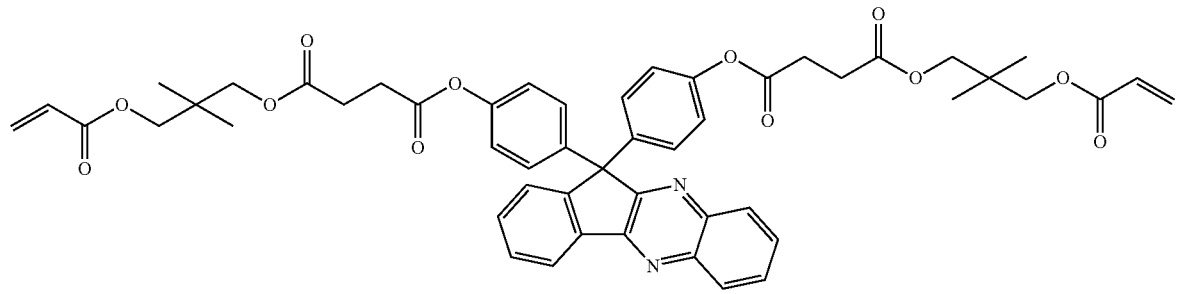
Compound 27
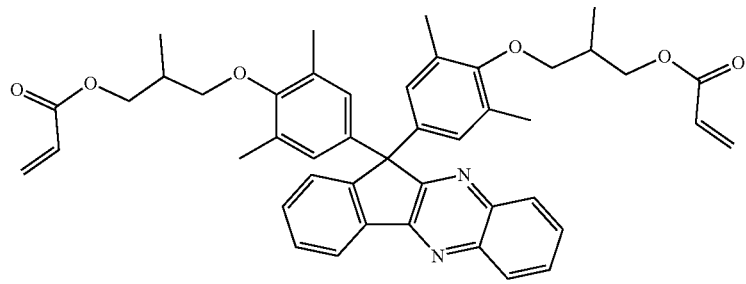
Compound 28
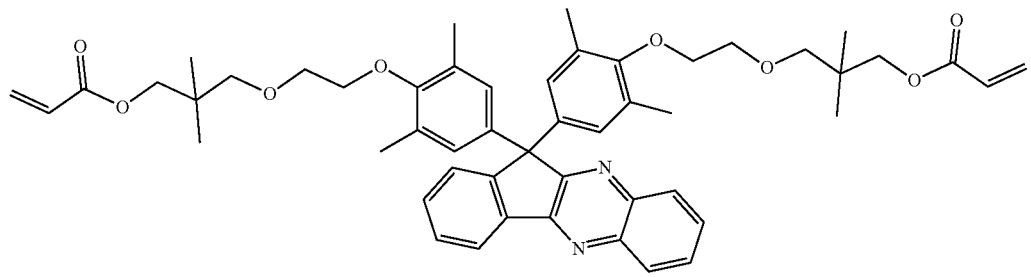
Compound 29
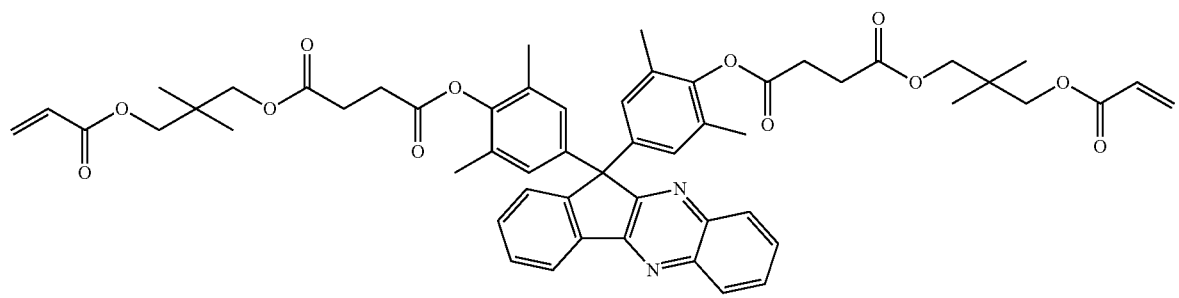
Compound 36
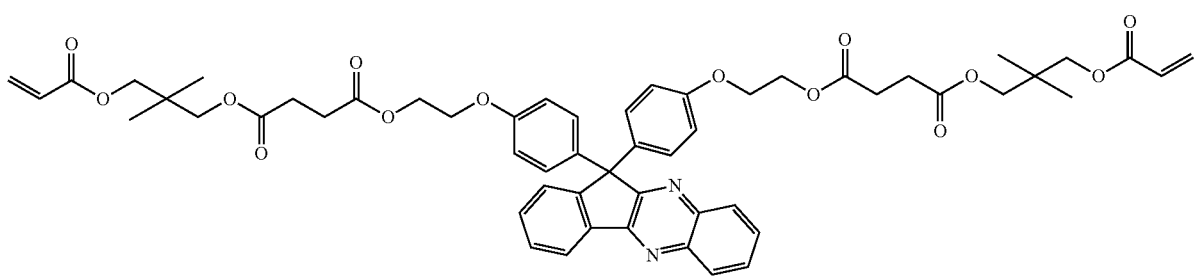

<Synthesis of Intermediate 1>

An intermediate 1 was synthesized according to the description in paragraph 0073 of JP2017-036249A.

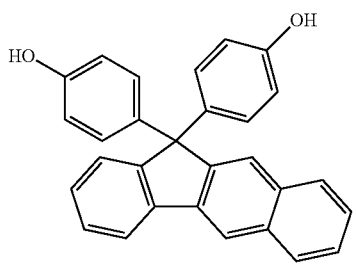

Intermediate 1

<Synthesis of Intermediate 2>

An intermediate 2 was synthesized according to the description in paragraph 0126 of WO2016/7-140245A.

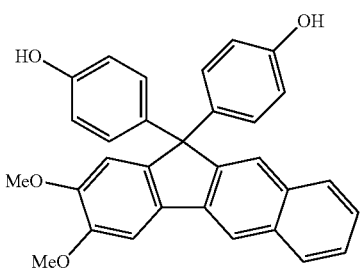

Intermediate 2

<Synthesis of Intermediate 3>

An intermediate 3 was synthesized according to the description in paragraph 0132 of WO2017/115649A.

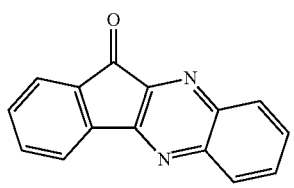

Intermediate 3

<Synthesis of Intermediate 4>

An intermediate 4 was synthesized according to the description in paragraph 0133 of WO2017/115649A.

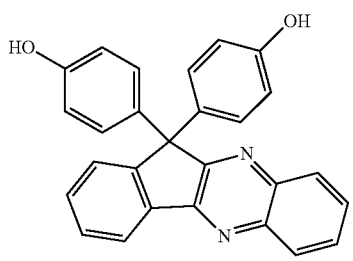

Intermediate 4

<Synthesis of Intermediate 5>

An intermediate 5 was synthesized according to the description in paragraph 0135 of WO2017/115649A.

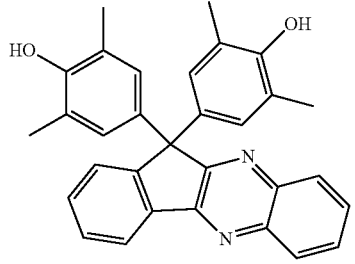

Intermediate 5

<Synthesis of Intermediate 6>

40 g of hydroxypropyl acrylate, 300 mL of dichloromethane, 3.8 g of N,N-dimethylaminopyridine, 33.8 g of succinic anhydride, and 200 mg of 2,6-di-t-butyl-4-methylphenol were mixed, and the internal temperature of the mixture was heated to 40° C. After stirring for 12 hours, the mixture was cooled to room temperature, 300 mL of water was added, and the mixture was stirred for 1 hour, followed by liquid separation. The collected organic layer was washed with 1 N hydrochloric acid water and saturated saline, and then dried over anhydrous sodium sulfate. Sodium sulfate was removed by filtration, and the solvent was removed by a rotary evaporator to obtain 70 g of an intermediate 6.

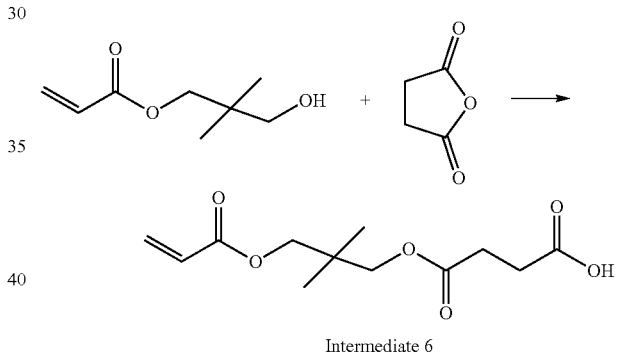

Intermediate 6

<Synthesis of Intermediate 7>

40 g of the intermediate 1, 24.5 g of propylene carbonate, 3.3 g of potassium carbonate, and 100 mL of dimethylacetamide were mixed and stirred at 110° C. for 6 hours. After checking disappearance of the raw materials, the mixture was cooled to 70° C., and 15 mL of 50 w/v % sodium hydroxide was added thereto. After stirring at 70° C. for 1 hour and checking disappearance of propylene carbonate, water and ethyl acetate were added, followed by liquid separation and concentration, and thereby 43.6 g of an intermediate 7 was obtained.

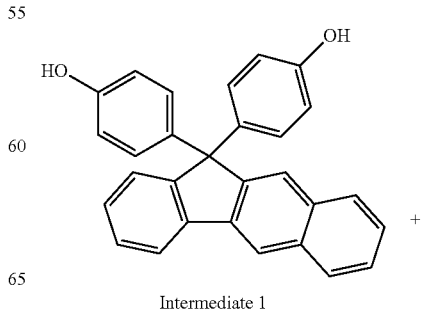

+

Intermediate 1

-continued

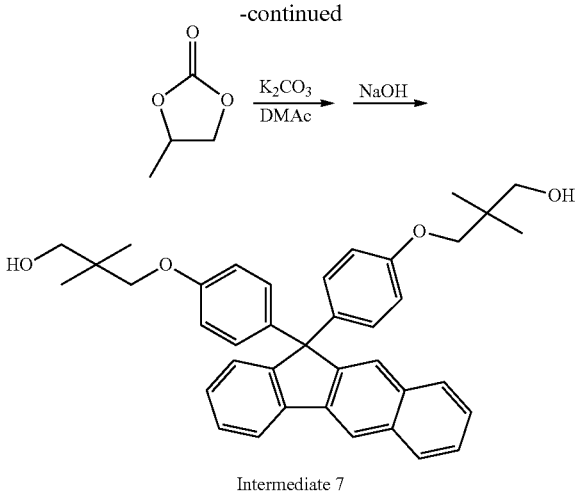

Intermediate 7

<Synthesis of Intermediate 8>
An intermediate 8 was synthesized in the same manner as the intermediate 7 except that the intermediate 1 was changed to the intermediate 2.

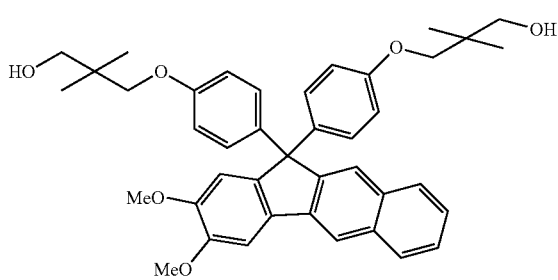

Intermediate 8

<Synthesis of Intermediate 9>
15.05 g of the intermediate 3, 44.8 g of 2-phenoxyethanol, 0.8 ml of dodecanethiol, and 40 mL of methanesulfonic acid were mixed and stirred at 110° C. for 1 hour. After checking disappearance of the intermediate 3, the mixture was cooled to 70° C. and diluted with a 3/1 (v/v) mixed solvent of cyclopentyl methyl ether/ethanol. After washing twice with water and once with a 10% aqueous sodium hydroxide solution, a small amount of hexane was added to the obtained organic layer and gradually cooled to precipitate crystals. The crystals were recovered by filtration and dried in a vacuum oven at 70° C., and thereby 17.5 g of an intermediate 9 was obtained.

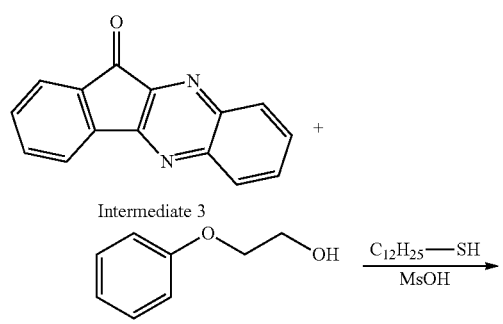

-continued

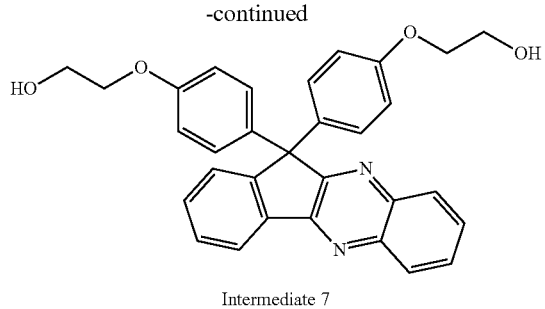

Intermediate 7

<Synthesis of Intermediate 10>
9.8 g of the intermediate 9 was dissolved in 50 ml of pyridine and cooled to 5° C. 11.8 g of p-toluenesulfonyl chloride was added little by little, and the mixture was stirred at 5° C. for 12 hours. After checking disappearance of the intermediate 9, the mixture was diluted with ethyl acetate and washed with water and saturated saline. The organic layer was dried over magnesium sulfate, and after removing magnesium sulfate by filtration, the residue was purified by silica gel column chromatography using hexane/ethyl acetate as a developing solvent, and thereby 9.1 g of the intermediate 10 was obtained.

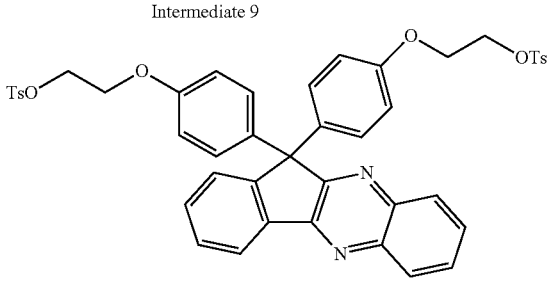

Intermediate 9

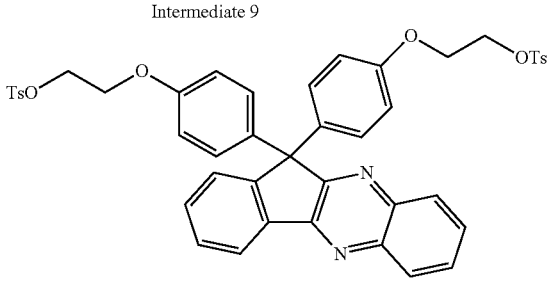

Intermediate 10

<Synthesis of Intermediate 11>
To a 200 mL three-neck flask, 120 mL of tetrahydrofuran (THF) and 1.35 g (oil-based, 60%) of sodium hydride (NaH) were added. After cooling in an ice bath, 4.7 g of neopentyl glycol was added and stirred at room temperature. After 1 hour, 9.0 g of the intermediate 10 was added and reacted at 60° C. for 3 hours. After cooling to room temperature, the reaction mixture was diluted with ethyl acetate, washed with water and saturated saline, and the organic layer was dried over magnesium sulfate. Magnesium sulfate was removed by filtration, hexane was added to the filtrate for recrystallization, and thereby 4.6 g of the intermediate 11 was obtained.

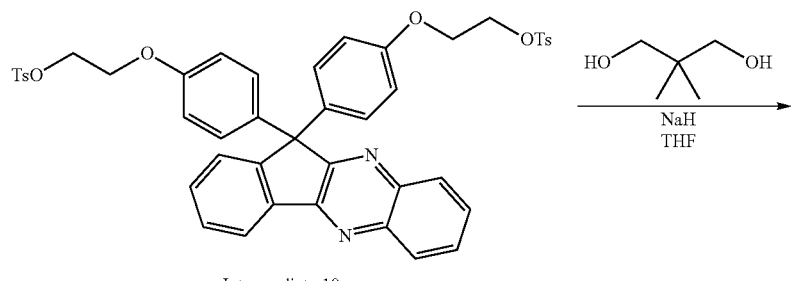

Intermediate 10

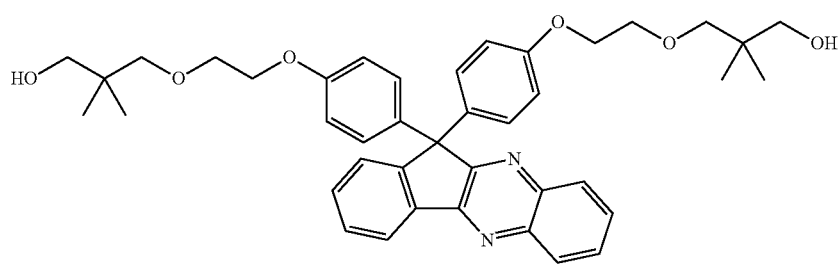

Intermediate 11

<Synthesis of Intermediate 12>

6.8 g of the intermediate 5, 5.0 g of 3-bromo-2-methyl-1-propanol, 6.2 g of potassium carbonate, and 50 mL of dimethylacetamide were mixed and stirred at 110° C. for 6 hours. After checking disappearance of the intermediate 5, the mixture was cooled to room temperature. The reaction mixture was diluted with ethyl acetate, washed with water and saturated saline, and the organic layer was dried over magnesium sulfate. After removing magnesium sulfate by filtration, the residue was purified by silica gel column chromatography using hexane/ethyl acetate as a developing solvent, and thereby 6.0 g of the intermediate 12 was obtained.

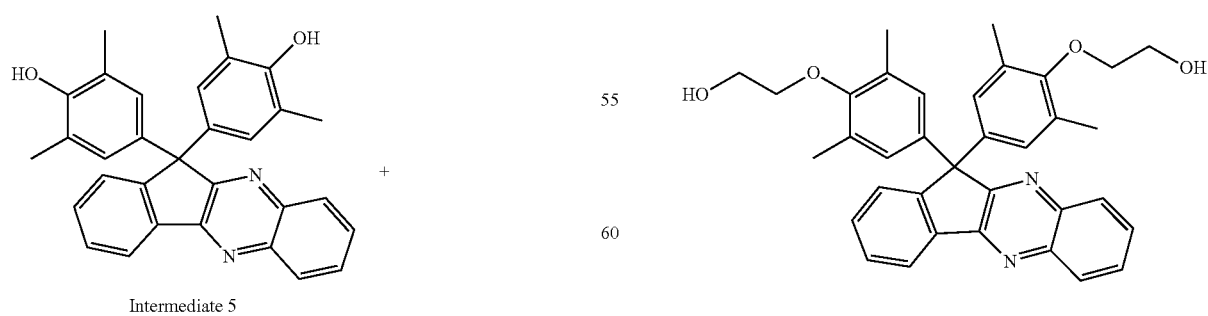

-continued

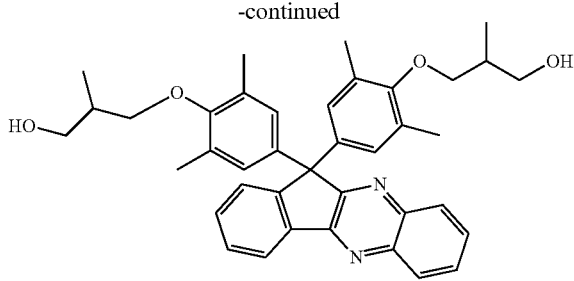

Intermediate 12

<Synthesis of Intermediate 13>

An intermediate 13 was synthesized in the same manner as the intermediate 12 except that 3-bromo-2-methyl-1-propanol was changed to 2-bromoethanol.

Intermediate 13

<Synthesis of Intermediate 14>

An intermediate 14 was synthesized in the same manner as the intermediate 10 except that the intermediate 9 was changed to the intermediate 13.

Intermediate 14

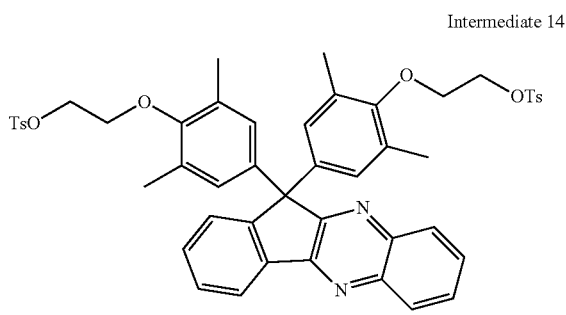 [SMILES: Cc1ccc(S(=O)(=O)OCCOc2c(C)cc(C3(c4cc(C)c(OCCOS(=O)(=O)c5ccc(C)cc5)c(C)c4)c4ccccc4-c4nc5ccccc5nc43)cc2C)cc1]

<Synthesis of Intermediate 15>

An intermediate 15 was synthesized in the same manner as the intermediate 11 except that the intermediate 10 was changed to the intermediate 14.

<Synthesis of Compound 14>

To a 300 mL three-neck flask, 8.0 g of the intermediate 1, 11.1 g of the intermediate 6, 240 mg of N,N-dimethylaminopyridine (DMAP), and 100 mL of dichloromethane were added and stirred in an ice bath for 10 minutes. 9.2 g of 1-(3-dimethylaminopropyl)-3-ethylcarbodiimide hydrochloride (EDAC-HCl) was added thereto, and the mixture was reacted at room temperature for 4 hours. The reaction solution was diluted with ethyl acetate, washed with water, an aqueous solution of saturated sodium bicarbonate, and saturated saline in this order, and then the organic layer was dried over magnesium sulfate. After removing magnesium sulfate by filtration, the residue was purified by silica gel column chromatography using hexane/ethyl acetate as a developing solvent, and thereby 12.6 g of a compound 14 was obtained. The $^1$H-NMR data of the compound 14 was as follows.

Intermediate 15

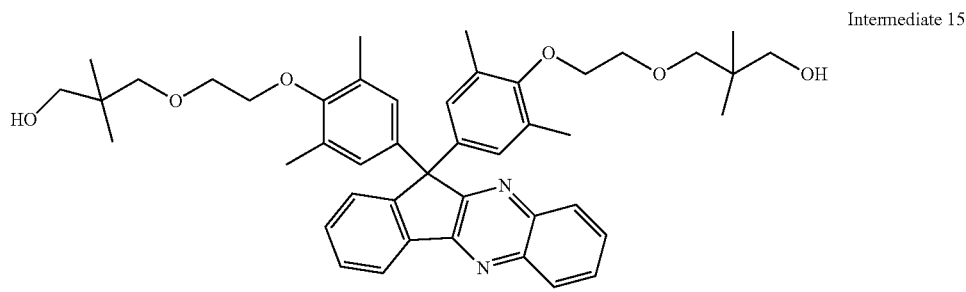 [SMILES: Cc1cc(C2(c3cc(C)c(OCCOCC(C)(C)CO)c(C)c3)c3ccccc3-c3nc4ccccc4nc32)cc(C)c1OCCOCC(C)(C)CO]

<Synthesis of Compound 1>

To a 200 mL three-neck flask equipped with a Dean-Stark apparatus, 20 g of the intermediate 7, 8.4 g of acrylic acid, 1.5 g of p-toluenesulfonic acid monohydrate, 100 mg of p-methoxyphenol, and 50 ml of toluene were weighed. A reaction was carried out in an oil bath at 120° C. for 8 hours while distilling off by-product water. The reaction solution was cooled to 50° C., diluted with ethyl acetate, and then washed twice with an aqueous solution of saturated sodium bicarbonate and once with pure water. The organic layer was dried over magnesium sulfate, and after removing magnesium sulfate by filtration, the residue was purified by silica gel column chromatography using hexane/ethyl acetate as a developing solvent, and thereby 17.8 g of a compound 1 was obtained. The $^1$H-NMR data of the compound 1 was as follows.

$^1$H-NMR (300 MHz, DMSO-d6): δ1.30-1.35 ppm (m, 6H), 4.05-4.30 ppm (m, 3H), 4.40-4.65 ppm (m, 1.5H), 5.15-5.30 ppm (m, 1.5H), 5.85-5.95 ppm (m, 2H), 6.15-6.25 ppm (m, 2H), 6.30-6.40 ppm (m, 2H), 6.90-6.95 ppm (d, 4H), 7.10-7.15 ppm (d, 4H), 7.30-7.50 ppm (m, 5H), 7.85-7.90 ppm (m, 2H), 7.95-8.05 ppm (m, 2H), 8.40 ppm (s, 1H)

<Synthesis of Compound 5>

A compound 5 was synthesized in the same manner as the compound 1 except that the intermediate 7 was changed to the intermediate 8. The $^1$H-NMR data of the compound 5 was as follows.

$^1$H-NMR (300 MHz, DMSO-d6): δ1.30-1.35 ppm (m, 6H), 3.72 ppm (s, 3H), 3.90 ppm (s, 3H), 4.05-4.30 ppm (m, 3H), 4.40-4.65 ppm (m, 1.5H), 5.15-5.30 ppm (m, 1.5H), 5.85-5.95 ppm (m, 2H), 6.15-6.25 ppm (m, 2H), 6.30-6.40 ppm (m, 2H), 6.80-6.88 ppm (d, 4H), 6.92 ppm (s, 1H), 7.10-7.15 ppm (d, 4H), 7.35-7.50 ppm (m, 2H), 7.68 ppm (s, 1H), 7.78 ppm (s, 1H), 7.80-7.95 ppm (m, 2H), 8.30 ppm (s, 1H)

$^1$H-NMR (300 MHz, DMSO-d6): δ1.18-1.30 ppm (m, 6H), 2.60-2.70 ppm (m, 4H), 2.75-2.85 ppm (m, 4H), 4.10-4.25 ppm (m, 4H), 5.05-5.15 ppm (m, 2H), 5.85-5.95 ppm (m, 2H), 6.05-6.15 ppm (m, 2H), 6.30-6.40 ppm (m, 2H), 6.95-7.05 ppm (d, 4H), 7.15-7.20 ppm (d, 4H), 7.30-7.50 ppm (m, 5H), 7.85-7.90 ppm (m, 2H), 7.95-8.05 ppm (m, 2H), 8.42 ppm (s, 1H)

<Synthesis of Compound 25>

A compound 25 was synthesized in the same manner as the compound 1 except that the intermediate 7 was changed to the intermediate 11. The $^1$H-NMR data of the compound 25 was as follows.

$^1$H-NMR (300 MHz, DMSO-d6): 0.90 ppm (s, 12H), 3.65-3.80 ppm (m, 8H), 4.05 ppm (s, 4H), 4.25-4.30 ppm (m, 4H), 5.85-5.95 ppm (m, 2H), 6.15-6.25 ppm (m, 2H), 6.30-6.40 ppm (m, 2H), 6.85-6.95 ppm (d, 4H), 7.05-7.15 ppm (d, 4H), 7.55-7.70 ppm (m, 3H), 7.75-7.90 ppm (m, 2H), 8.00-8.10 ppm (d, 1H), 8.15-8.25 ppm (m, 2H)

<Synthesis of Compound 26>

A compound 26 was synthesized in the same manner as the compound 14 except that the intermediate 1 was changed to the intermediate 4. The $^1$H-NMR data of the compound 26 was as follows.

$^1$H-NMR (300 MHz, DMSO-d6): δ1.18-1.30 ppm (m, 6H), 2.60-2.70 ppm (m, 4H), 2.75-2.85 ppm (m, 4H), 4.10-4.25 ppm (m, 4H), 5.05-5.15 ppm (m, 2H), 5.85-5.95 ppm (m, 2H), 6.15-6.25 ppm (m, 2H), 6.30-6.40 ppm (m, 2H), 7.00-7.10 ppm (d, 4H), 7.20-7.30 ppm (d, 4H), 7.55-7.70 ppm (m, 3H), 7.75-7.90 ppm (m, 2H), 8.05-8.15 ppm (d, 1H), 8.20-8.30 ppm (m, 2H)

<Synthesis of Compound 27>

A compound 27 was synthesized in the same manner as the compound 1 except that the intermediate 7 was changed to the intermediate 12. The $^1$H-NMR data of the compound 27 was as follows.

$^1$H-NMR (300 MHz, DMSO-d6): δ0.92-1.00 ppm (d, 6H), 2.10 ppm (s, 12H), 2.20-2.30 ppm (m, 2H), 3.40-3.50 ppm (m, 4H), 4.00-4.20 ppm (m, 4H), 5.90-6.00 ppm (m, 2H), 6.15-6.25 ppm (m, 2H), 6.30-6.40 ppm (m, 2H), 6.85-6.95 ppm (s, 4H), 7.60-7.70 ppm (m, 3H), 7.75-7.90 ppm (m, 2H), 8.00-8.10 ppm (d, 1H), 8.15-8.25 ppm (m, 2H)

<Synthesis of Compound 28>

A compound 28 was synthesized in the same manner as the compound 1 except that the intermediate 7 was changed to the intermediate 15. The $^1$H-NMR data of the compound 28 was as follows.

$^1$H-NMR (300 MHz, DMSO-d6): δ0.90 ppm (s, 12H), 2.10 ppm (s, 12H), 3.65-3.80 ppm (m, 8H), 64.05 ppm (s, 4H), 4.25-4.30 ppm (m, 4H), 5.90-6.00 ppm (m, 2H), 6.15-6.25 ppm (m, 2H), 6.30-6.40 ppm (m, 2H), 6.85-6.95 ppm (s, 4H), 7.60-7.70 ppm (m, 3H), 7.75-7.90 ppm (m, 2H), 8.00-8.10 ppm (d, 1H), 8.15-8.25 ppm (m, 2H)

<Synthesis of Compound 29>

A compound 29 was synthesized in the same manner as the compound 14 except that the intermediate 1 was changed to the intermediate 5. The $^1$H-NMR data of the compound 29 was as follows.

$^1$H-NMR (300 MHz, DMSO-d6): δ1.18-1.30 ppm (m, 6H), 2.10 ppm (s, 12H), 2.60-2.70 ppm (m, 4H), 2.75-2.85 ppm (m, 4H), 4.10-4.25 ppm (m, 4H), 5.05-5.15 ppm (m, 2H), 5.85-5.95 ppm (m, 2H), 6.05-6.15 ppm (m, 2H), 6.30-6.40 ppm (m, 2H), 6.95-7.05 ppm (s, 4H), 7.55-7.70 ppm (m, 3H), 7.75-7.90 ppm (m, 2H), 8.05-8.15 ppm (d, 1H), 8.20-8.30 ppm (m, 2H)

<Synthesis of Compound 36>

A compound 36 was synthesized in the same manner as the compound 14 except that the intermediate 1 was changed to the intermediate 9. The $^1$H-NMR data of the compound 36 was as follows.

$^1$H-NMR (300 MHz, DMSO-d6): δ1.18-1.30 ppm (m, 6H), 2.60-2.70 ppm (m, 4H), 2.75-2.85 ppm (m, 4H), 4.10-4.30 ppm (m, 8H), 4.35-4.45 ppm (m, 4H), 5.05-5.15 ppm (m, 2H), 5.85-5.95 ppm (m, 2H), 6.15-6.25 ppm (m, 2H), 6.30-6.40 ppm (m, 2H), 6.85-6.95 ppm (d, 4H), 7.05-7.15 ppm (d, 4H), 7.55-7.70 ppm (m, 3H), 7.75-7.90 ppm (m, 2H), 8.00-8.10 ppm (d, 1H), 8.15-8.25 ppm (m, 2H)

(Preparation of Curable Composition)

Respective components were mixed to obtain the composition shown in Table 2, and the mixture was stirred to make it homogeneous to prepare a curable composition. The prepared curable composition was sealed in a brown glass bottle and stored in a refrigerator at −5° C.

<Component A>

As the component A, the compound synthesized above was used. In addition, the following comparative compounds 1-1 and 1-2 were used as comparative compounds.

Comparative Compound 1-1

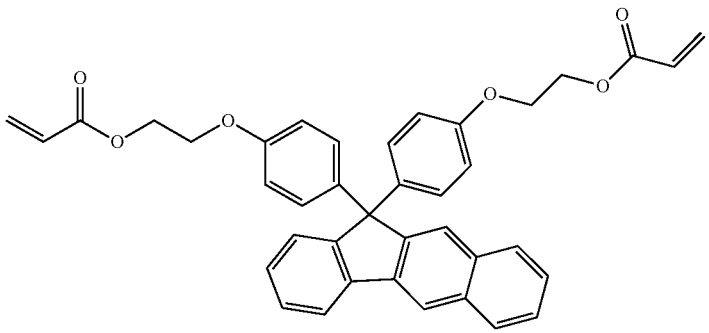

Comparative Compound 1-2

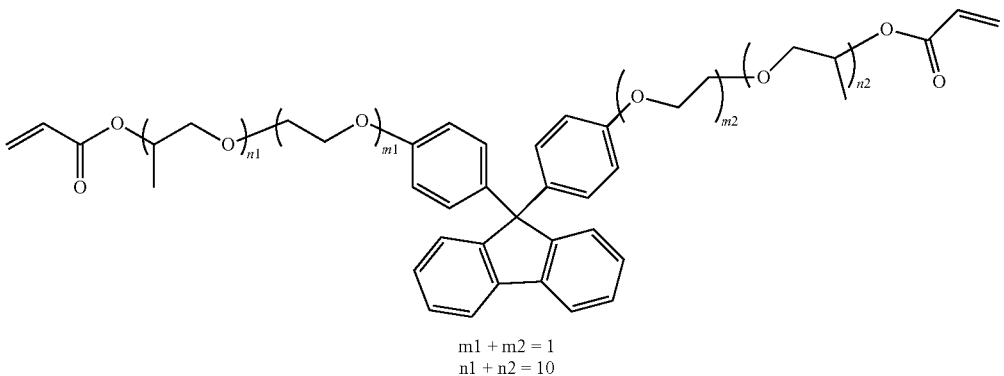

m1 + m2 = 1
n1 + n2 = 10

<Component B>

The following compound monomer 1 (a (meth)acrylate monomer) was used.

Monomer 1

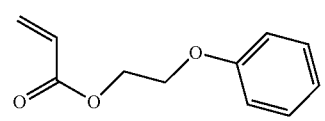

<Non-Conjugated-Vinylidene-Group-Containing Compound>

The following compound (β-caryophyllene, manufactured by Inoue Perfumery Mfg. Co., Ltd.) was used as the non-conjugated-vinylidene-group-containing compound. There is no particular restriction on the optical isomers thereof.

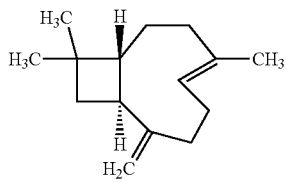

<Photoradical Polymerization Initiator>

The following compound (IRGACURE 819, manufactured by BASF Corporation) was used as the photoradical polymerization initiator.

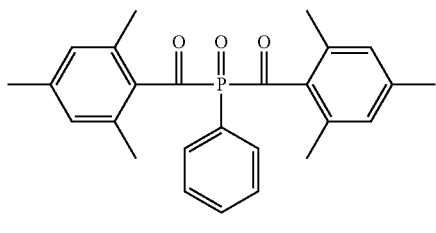

Irgacure819

<Thermal Radical Polymerization Initiator>

The following compounds were used as the thermal radical polymerization initiator.
PERBUTYL O: manufactured by NOF Corporation
PERCUMYL H-80: manufactured by NOF Corporation

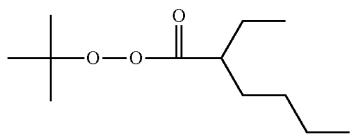

PERBUTYL O

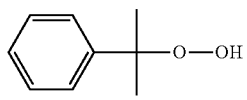

PERCUMYL H-80

<Mold Release Agent>
JP-506H manufactured by Johoku Chemical Co., Ltd.

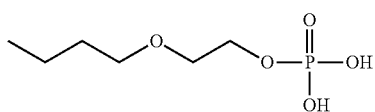

(Evaluation)
<Refractive Index and Abbe Number>

The curable compositions obtained in the examples and comparative examples were poured into a transparent glass mold having a diameter of 20 mm and a thickness of 2 mm, and heated to 200° C. in an atmosphere having an oxygen concentration of 1% or less to produce a thermally cured product. The obtained thermally cured product was processed into a V-shaped block. Thereafter, a refractive index and an Abbe number (vd) were measured using a Kalnew precision refractometer KPR-2000 (manufactured by Shimadzu Device Corporation). The measurement was performed three times for each sample at 25° C., and an average value was taken as a measurement result.

$$vd=(nd-1)/(nF-nC)$$

Where, nd represents a refractive index at a wavelength of 587.56 nm, nF represents a refractive index at a wavelength of 486.13 nm, and nC represents a refractive index at a wavelength of 656.27 nm.

In addition, according to the following method, evaluation of moisture-heat resistance of each sample was also performed.

<Evaluation of Moisture-Heat Resistance>

Each sample whose refractive index (nd) was measured was placed in a constant temperature and humidity chamber maintained at 85° C. and a relative humidity of 85%, stored for 24 hours, and then taken out. Next, after being allowed to stand at 25° C. and relative humidity 60% for 1 hour, a refractive index (nd) was measured, and an amount of change in the refractive index before and after the moisture-heat test was evaluated in the following four grades, A to D. Rank A and rank B were acceptable levels.

Rank A: A change in refractive index before and after the moisture-heat test was 0.0003 or less
Rank B: A change in refractive index before and after the moisture-heat test was more than 0.0003 and 0.0005 or less
Rank C: A change in refractive index before and after the moisture-heat test was more than 0.0005 and 0.001 or less
Rank D: A change in refractive index before and after the moisture-heat test was more than 0.001

<Production of Compound Lens>

200 mg of the curable compositions obtained in the examples and comparative examples were injected into a molding mold whose surface was treated with chromium nitride (the surface in contact with the curable composition had an aspheric shape), the entire surface of the curable composition that is not in contact with the molding mold was covered with a transparent glass lens (glass material BK-7, convex lens with a diameter of 33 mm, a center thickness of 3 mm, a radius of curvature of the surface in contact with the curable composition=44.3 mm, a radius of curvature of the surface not in contact with the curable composition=330.9 mm), and the curable composition was expanded to have a diameter of 30 mm. After this state, irradiation of ultraviolet light of 300 mJ/cm$^2$ was performed from above the glass lens using an Execure 3000 (manufactured by Hoya Corporation). Next, while maintaining the state sandwiched between the molding mold and the glass lens, the temperature was raised to 200° C. while applying a pressure of 0.196 MPa (2 kgf/cm$^2$) to further performing curing (a step of molding a cured product). Subsequently, after cooling the mold temperature to 180° C., the cured product of the curable composition and the molding mold were separated at a speed of 0.05 mm/sec to produce a compound lens (a step of separating a mold). In order to use for the following evaluation, the above step was repeated 100 times to produce 100 compound lenses.

Using the curable composition within 15 days after the preparation and the curable composition stored in the refrigerator for 12 months, 100 compound lenses were respectively and similarly produced and used for evaluation.

<Appearance Inspection>

The appearance of each compound lens produced as described above was evaluated using a digital microscope (trade name: VHX-1000, manufactured by Keyence Corporation).

Products with a minute foreign matter failure (irregularities) on the surface of the compound lens were regarded as defective products, and products without a minute foreign matter failure (irregularities) were regarded as non-defective products. The produced 100 compound lenses were evaluated, and the percentage of non-defective products among them was evaluated as a non-defective rate and evaluated according to the following standards. Rank A and rank B were acceptable levels.

Rank A: The non-defective rate was 90% or more.
Rank B: The non-defective rate was 70% or more and less than 90%.
Rank C: The non-defective rate was 50% or more and less than 70%.
Rank D: The non-defective rate was less than 50%.

TABLE 2

|  |  | Example 1 | Example 2 | Example 3 | Example 4 | Example 5 | Example 6 | Example 7 | Example 8 | Example 9 |
|---|---|---|---|---|---|---|---|---|---|---|
| Component A | Compound (1) | 70.9 | 75.6 | | | | | | | |
| | Compound (5) | | | | | | | | | |
| | Compound (14) | | | 70.9 | | | | | | |
| | Compound (25) | | | | 70.9 | | | | | |
| | Compound (26) | | | | | 70.9 | 70.9 | 83.2 | | |
| | Compound (27) | | | | | | | | | |
| | Compound (28) | | | | | | | | 70.9 | |
| | Compound (29) | | | | | | | | | 70.9 |
| | Compound (36) | | | | | | | | | |
| | Comparative Compound 1-1 | | | | | | | | | |
| | Comparative Compound 1-2 | | | | | | | | | |
| (Meth)acrylate monomer | Monomer 1 | 22.7 | 18.0 | 22.7 | 22.7 | 22.7 | 22.7 | 10.4 | 22.7 | 22.7 |
| Non-conjugated-vinylidene-group-containing compound | β-Caryophyllene | 4.5 | 4.5 | 4.5 | 4.5 | 4.5 | 4.5 | 4.5 | 4.5 | 4.5 |
| Photo-radical polymerization initiator | Irgacure 819 | 0.1 | 0.1 | 0.1 | 0.1 | 0.1 | 0.1 | 0.1 | 0.1 | 0.1 |
| Thermal radical polymerization initiator | PERBUTYL O | 1.0 | 1.0 | 1.0 | 1 | 1 | 1 | 1 | 1 | 1 |
| | PERCUMYL H-80 | 0.7 | 0.7 | 0.7 | 0.7 | 0.7 | 0.7 | 0.7 | 0.7 | 0.7 |
| Mold release agent | JP-506H | 0.1 | 0.1 | 0.1 | 0.1 | 0.1 | 0.1 | 0.1 | 0.1 | 0.1 |
| Physical properties of cured product | nd | 1.621 | 1.627 | 1.634 | 1.612 | 1.638 | 1.629 | 1.636 | 1.630 | 1.621 |
| | vd | 23.2 | 22.9 | 20.9 | 23.7 | 20.0 | 20.7 | 19.9 | 20.5 | 21.0 |
| | Moisture-heat resistance | A | A | A | B | A | B | B | A | A |
| Evaluation of compound lens (inspection of external appearance) | Within 15 days after preparation | A | A | A | A | A | A | A | A | A |
| | After 12 months | A | A | A | A | B | A | A | B | B |

|  |  | Example 10 | Example 11 | Example 12 | Example 13 | Comparative Example 1 | Comparative Example 2 | Comparative Example 3 |
|---|---|---|---|---|---|---|---|---|
| Component A | Compound (1) | | | | | | | |
| | Compound (5) | | | | | | | |
| | Compound (14) | | | | | | | |
| | Compound (25) | | | | | | | |
| | Compound (26) | | | | | | | |
| | Compound (27) | | | | | | | |
| | Compound (28) | | | | | | | |
| | Compound (29) | 70.9 | 61.6 | 52.1 | | | | |
| | Compound (36) | | | | 70.9 | | | |
| | Comparative Compound 1-1 | | | | | 70.9 | 75.6 | |
| | Comparative Compound 1-2 | | | | | | | 93.6 |

TABLE 2-continued

| | | | | | | | | |
|---|---|---|---|---|---|---|---|---|
| (Meth)acrylate monomer | Monomer 1 | 22.7 | 32.0 | 41.5 | 22.7 | 22.7 | 18 | |
| Non-conjugated-vinylidene-group-containing compound | β-Caryophyllene | 4.5 | 4.5 | 4.5 | 4.5 | 4.5 | 4.5 | 4.5 |
| Photo-radical polymerization initiator | Irgacure 819 | 0.1 | 0.1 | 0.1 | 0.1 | 0.1 | 0.1 | 0.1 |
| Thermal radical polymerization initiator | PERBUTYL O | 1 | 1 | 1 | 1 | 1 | 1 | 1 |
| | PERCUMYL H-80 | 0.7 | 0.7 | 0.7 | 0.7 | 0.7 | 0.7 | 0.7 |
| Mold release agent | JP-506H | 0.1 | 0.1 | 0.1 | 0.1 | 0.1 | 0.1 | 0.1 |
| Physical properties of cured product | nd | 1.620 | 1.609 | 1.597 | 1.631 | 1.627 | 1.633 | 1.541 |
| | vd | 21.3 | 23.1 | 25.0 | 20.2 | 23.1 | 22.8 | 28.8 |
| | Moisture-heat resistance | A | A | A | A | A | A | D |
| Evaluation of compound lens (inspection of external appearance) | Within 15 days after preparation | A | A | A | A | B | B | A |
| | After 12 months | A | A | A | A | C | D | A |

In the table, a mass of each component is mass %.

As can be seen from Comparative Example 3, the comparative compound 1-2 has a large Abbe number of the cured product and poor moisture-heat resistance. As can be seen from Comparative Examples 1 and 2, the comparative compound 1-1 was able to reduce the Abbe number of the cured product by increasing a proportion of the component (A) therein, but the appearance of the compound lens produced after storage over time deteriorated.

On the other hand, as can be seen from Examples 1 and 2, even in a case where a proportion of the component (A) was increased in the compound of the embodiment of the present invention (for example, the compound 1), the appearance of the compound lens produced after storage over time was favorable.

As can be seen from the comparison between Examples 1 and 3 (the compound 1 and the compound 5), in the partial structure A, A-5 was more advantageous for lowering an Abbe number than A-1, and it is presumed that substitution of a methoxy group contributes to lower an Abbe number.

Based on the comparison of Examples 4 and 6 (the compound 14 and the compound 26), it can be seen that A-7 is more advantageous for lowering an Abbe number than A-1 in the partial structure A.

In the examples using the compound containing structural isomers in which positions of substitution of an alkyl group to a linear alkylene group are different, evaluation of the appearance after long-term storage was higher than those the examples using the compounds not containing the structural isomers (the compounds 25, 27, and 28) (respectively Examples 5, 8, and 9).

As can be seen from the comparison between Example 6 (the compound 26) and Example 10 (the compound 29), it could be understood that moisture-heat resistance could be improved by converting the partial structure B to B-3 (a dimethylphenyl type) in the compound having the partial structure C-7 (ester).

What is claimed is:
1. A compound represented by General Formula (A):

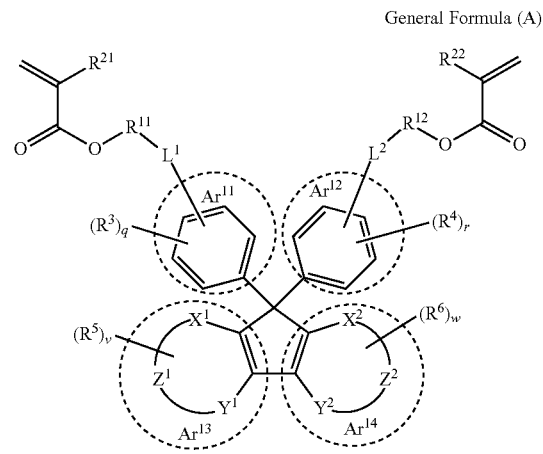

General Formula (A)

in General Formula (A), $Ar^{11}$ and $Ar^{12}$ each independently represent an aryl group containing a benzene ring surrounded by a broken line or a heteroaryl group containing a benzene ring surrounded by a broken line as one of rings constituting a fused ring,
$X^1$, $Y^1$, $X^2$, and $Y^2$ each independently represent an oxygen atom, a sulfur atom, a nitrogen atom, or a carbon atom; $Z^1$ represents an atomic group which forms a 5- to 7-membered aromatic ring together with $X^1$—C=C—$Y^1$, and which contains at least one selected from an oxygen atom, a sulfur atom, a nitrogen atom, or a carbon atom; and $Z^2$ represents an atomic group which forms a 5- to 7-membered aromatic ring together with $X^2$—C=C—$Y^2$, and which contains at least one selected from an oxygen atom, a sulfur atom, a nitrogen atom, or a carbon atom, Ar$^{13}$ and Ar$^{14}$ each independently represent an arylene group containing an aromatic ring surrounded by a broken line or a heteroarylene group containing an aromatic ring surrounded by a broken line, where at least one of Ar$^{13}$ or Ar$^{14}$ is a group other than a phenylene group, R$^3$ to R$^6$ each independently represent a substituent; q and r each independently are an integer of 0 to 4; v is an integer of 0 or more, where a maximum number of v is a maximum number of substituents capable of being substituted on the ring formed by X$^1$—C=C—Y$^1$ and Z$^1$; and w is an integer of 0 or more, where a maximum number of w is a maximum number of substituents capable of being substituted on the ring formed by X$^2$—C=C—Y$^2$ and Z$^2$, L$^1$ and L$^2$ each independently represent a single bond, an oxygen atom, a sulfur atom, or an ester bond, R$^{11}$ and R$^{12}$ each independently represent a divalent linking group containing a branched alkylene group in which one or more alkyl groups are substituted on a linear alkylene group, R$^{21}$ and R$^{22}$ each independently represent a hydrogen atom or a methyl group, and in a case where Ar$^{11}$ to Ar$^{14}$ each independently are a fused ring group containing an aromatic ring surrounded by a broken line as one of rings constituting the fused ring, a group having L$^1$ as a linking group, a group having L$^2$ as a linking group, and R$^3$ to R$^6$ each independently may be substituted on the aromatic ring surrounded by the broken line, or may be substituted on another ring constituting the fused ring than the aromatic ring surrounded by the broken line.

2. The compound according to claim 1, wherein Ar$^{11}$ and Ar$^{12}$ each are a phenyl group.

3. The compound according to claim 1, wherein at least one of Ar$^{13}$ or Ar$^{14}$ is a fused ring group containing the aromatic ring surrounded by the broken line as one of the rings constituting the fused ring.

4. The compound according to claim 1, wherein X$^1$ and Y$^1$, or X$^2$ and Y$^2$ each are a nitrogen atom.

5. The compound according to claim 1, wherein at least one of L$^1$ or L$^2$ is an ester bond.

6. The compound according to claim 1, wherein the branched alkylene group is a mixture of structural isomers in which positions at which the one or more alkyl groups are substituted on the linear alkylene group are different.

7. The compound according to claim 1, which is selected from the following compounds.

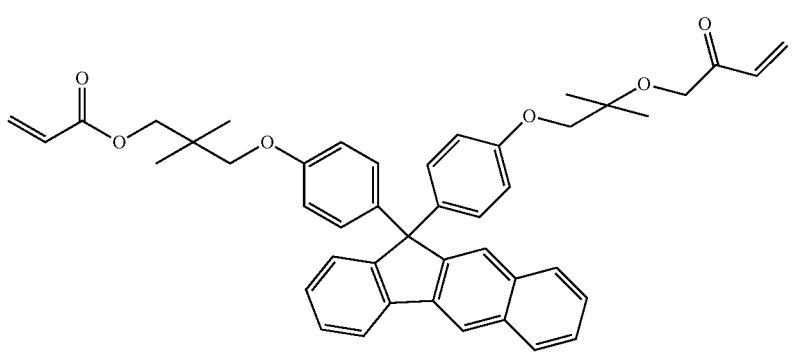

Compound 1

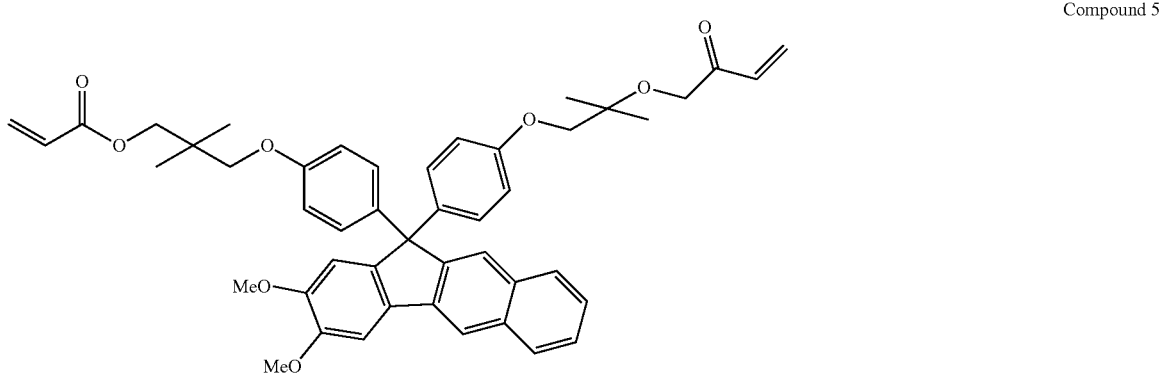

Compound 5

-continued
Compound 14
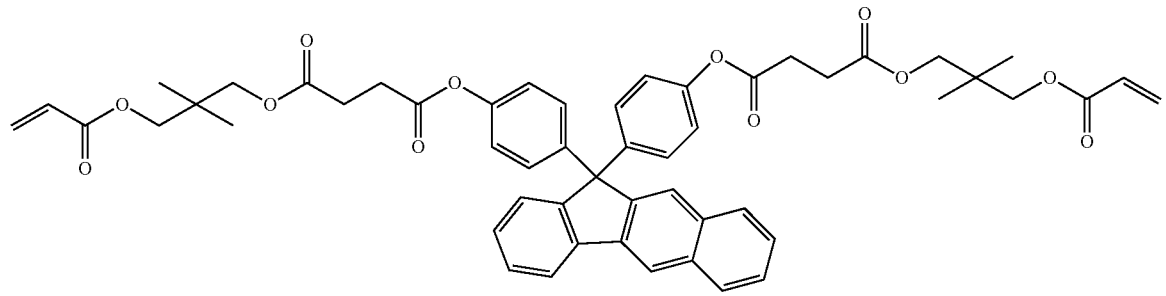
Compound 25
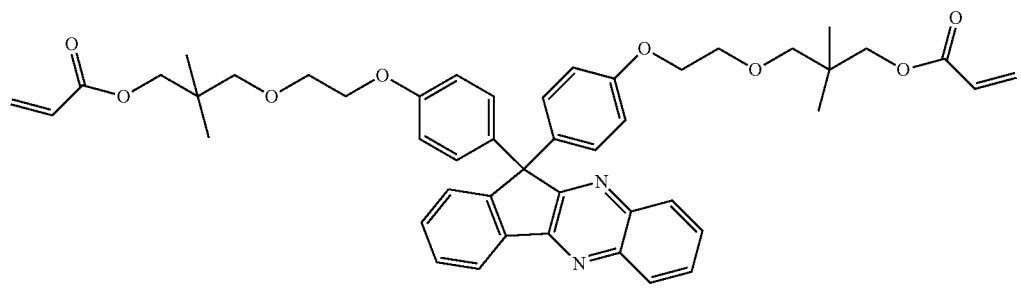
Compound 26
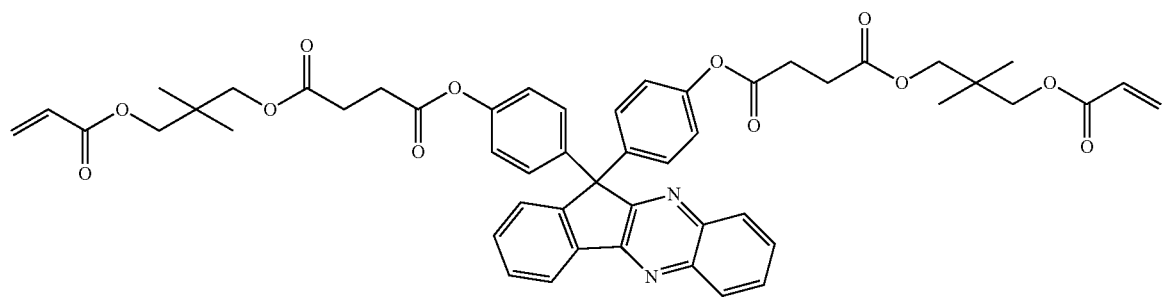
Compound 27
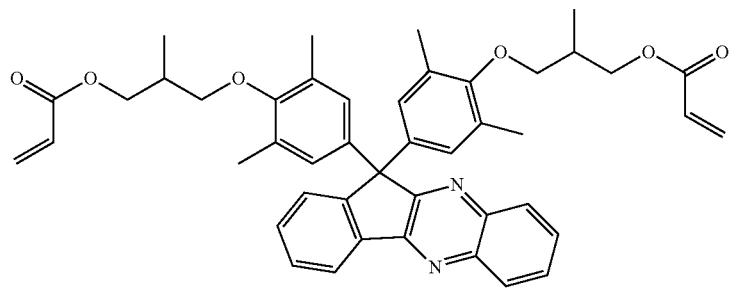
Compound 28
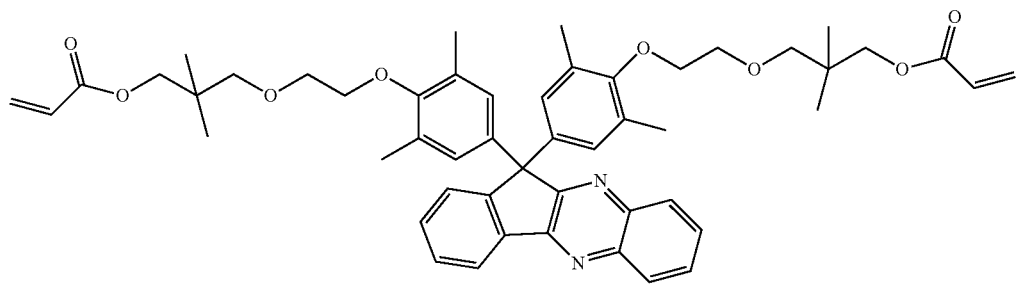

Compound 29

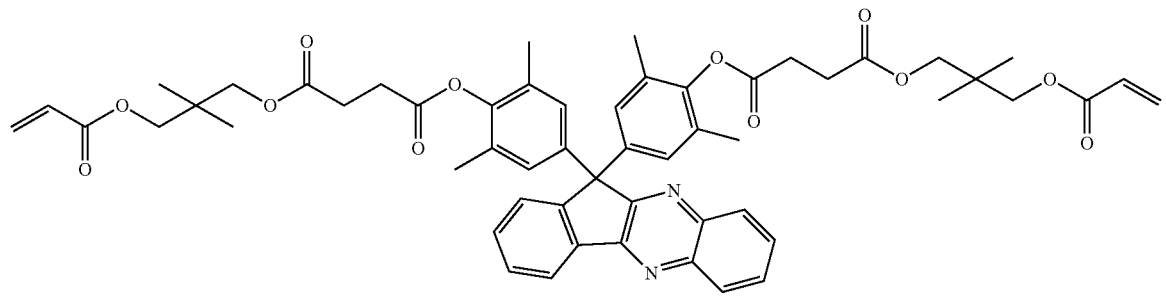

Compound 36

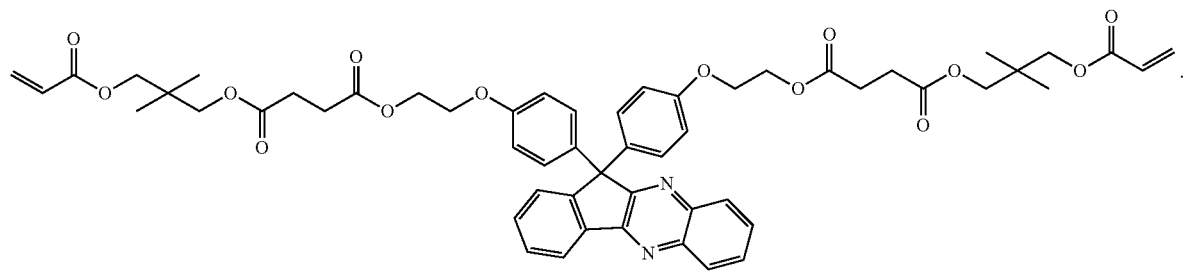

8. A curable composition comprising the compound according to claim 1.

9. A curable composition comprising the compound according to claim 7.

10. The curable composition according to claim 8, further comprising a non-conjugated-vinylidene-group-containing compound.

11. The curable composition according to claim 9, further comprising a non-conjugated-vinylidene-group-containing compound.

12. The curable composition according to claim 8, further comprising a hydroperoxide compound as a thermal radical polymerization initiator.

13. The curable composition according to claim 10, further comprising a hydroperoxide compound as a thermal radical polymerization initiator.

14. A semi-cured product of the curable composition according to claim 8, wherein a complex viscosity at 25° C. and a frequency of 10 Hz is $10^5$ to $10^8$ mPa·s.

15. A cured product of the curable composition according to claim 8.

16. A cured product of the curable composition according to claim 9.

17. An optical member comprising the cured product according to claim 15.

18. An optical member comprising the cured product according to claim 16.

19. A lens comprising the cured product according to claim 15.

20. A lens comprising the cured product according to claim 16.

* * * * *